US011578103B2

(12) United States Patent
Chang et al.

(10) Patent No.: US 11,578,103 B2
(45) Date of Patent: Feb. 14, 2023

(54) NUCLEIC ACIDS ENCODING ZIKA VIRUS-LIKE PARTICLES AND THEIR USE IN ZIKA VIRUS VACCINES AND DIAGNOSTIC ASSAYS

(71) Applicant: The U.S.A., as represented by the Secretary, Department of Health and Human Services, Bethesda, MD (US)

(72) Inventors: Gwong-Jen J. Chang, Fort Collins, CO (US); Brent S. Davis, Fort Collins, CO (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 91 days.

(21) Appl. No.: 17/168,889

(22) Filed: Feb. 5, 2021

(65) Prior Publication Data

US 2021/0188917 A1 Jun. 24, 2021

Related U.S. Application Data

(62) Division of application No. 16/309,288, filed as application No. PCT/US2017/036762 on Jun. 9, 2017, now Pat. No. 10,947,277.

(60) Provisional application No. 62/349,537, filed on Jun. 13, 2016.

(51) Int. Cl.
*A61K 39/12* (2006.01)
*C07K 14/005* (2006.01)
*A61P 31/14* (2006.01)
*C12N 15/86* (2006.01)
*G01N 33/569* (2006.01)
*A61K 39/00* (2006.01)
*C07K 14/18* (2006.01)

(52) U.S. Cl.
CPC ............ *C07K 14/005* (2013.01); *A61K 39/12* (2013.01); *A61P 31/14* (2018.01); *C12N 15/86* (2013.01); *G01N 33/56983* (2013.01); *A61K 2039/53* (2013.01); *C07K 14/1825* (2013.01); *C12N 2710/10343* (2013.01); *C12N 2710/16143* (2013.01); *C12N 2770/24122* (2013.01); *C12N 2770/24123* (2013.01); *C12N 2770/24134* (2013.01); *C12N 2830/60* (2013.01); *Y02A 50/30* (2018.01)

(58) Field of Classification Search
CPC ...................... A61K 39/12; C12N 2770/24122
See application file for complete search history.

(56) References Cited

U.S. PATENT DOCUMENTS

| 7,227,011 | B2 * | 6/2007 | Chang ............. G01N 33/56983 424/218.1 |
| 7,417,136 | B1 | 8/2008 | Chang |
| 7,521,177 | B2 | 4/2009 | Chang |
| 7,632,510 | B2 | 12/2009 | Chang |
| 7,662,394 | B2 | 2/2010 | Chang |
| 7,906,292 | B2 | 3/2011 | Chang et al. |
| 8,105,609 | B2 | 1/2012 | Chang |
| 8,221,768 | B2 | 7/2012 | Chang |
| 8,232,379 | B2 | 7/2012 | Chang |
| 8,728,488 | B2 | 5/2014 | Chang |
| 9,000,141 | B2 | 4/2015 | Chang et al. |
| 9,284,356 | B2 | 3/2016 | Chang et al. |
| 10,092,637 | B2 * | 10/2018 | Chang ....................... C12N 7/00 |
| 2012/0135035 | A1 * | 5/2012 | Simmons ................ A61P 37/02 424/199.1 |
| 2017/0014502 | A1 * | 1/2017 | Sumathy ................. A61K 39/12 |
| 2017/0252425 | A1 | 9/2017 | Akahata et al. |
| 2018/0177859 | A1 | 6/2018 | Galarza et al. |
| 2019/0309025 | A1 | 10/2019 | Chang et al. |

FOREIGN PATENT DOCUMENTS

| WO | WO 02/081754 | 10/2002 |
| WO | WO 2006/025990 | 3/2006 |
| WO | WO 2006/025990 A2 * | 3/2006 |
| WO | WO 2016/210127 | 12/2016 |
| WO | WO 2017/009873 | 1/2017 |
| WO | WO 2017/015463 | 1/2017 |
| WO | WO 2017/109222 | 6/2017 |

OTHER PUBLICATIONS

Abbink et al., "Protecrive Efficacy of Multiple Vaccine Platforms Against Zika Virus Challenge in Rhesus Monkeys," *Science*, vol. 353:1129-1132, 2016.
Davis et al., "West Nile Virus Recombinant DNA Vaccine Protects Mouse and Horse from Virus Challenge and Expresses in Vitro a Noninfectious Recombinant Antigen that can be used in Enzyme-Linked Immunosorbent Assays," *J. Virol.*, vol. 75:4040-4047, 2001.
Faye et al., "Molecular Evolution of Zika Virus during its Emergence in the 20th Century," *PLoS Negl. Trop. Dis.*, vol. 8:e2636, 2014.
GenBank Accession No. NC 012532, Feb. 8, 2016.
GenBank Accession No. KU321639.1, Mar. 16, 2016.
Kuno et al., "Full-Length Sequencing and Genomic Characterization of Bagaza, Kedougou, and Zika Viruses," *Arch. Virol.*, vol. 152:687-696, 2007.
Larocca et al., "Vaccine Protection against Zika Virus from Brazil," *Nature*, vol. 536:474-478, 2016.

(Continued)

*Primary Examiner* — Jeffrey S Parkin
(74) *Attorney, Agent, or Firm* — Klarquist Sparkman, LLP

(57) ABSTRACT

Transcriptional units encoding Zika virus (ZIKV) premembrane (prM) and envelope (E) proteins, which upon translation form Zika virus-like particles (VLPs), are described. Use of the transcriptional units and VLPs in three different ZIKV vaccine platforms is described. Immunoassay-based detection methods using ZIKV VLPs are described for the diagnosis of ZIKV infection.

20 Claims, 7 Drawing Sheets

Specification includes a Sequence Listing.

(56) References Cited

OTHER PUBLICATIONS

Malone et al., "Zika Virus: Medical Countermeasure Development Challenges," *PLoS Negl. Trop. Dis.*, vol. 10:e0004530, 2016.
Wang et al., "From Mosquitos to Humans: Genetic Evolution of Zika Virus," *Cell Host & Microbe*, vol. 19:561-568, 2016.

* cited by examiner

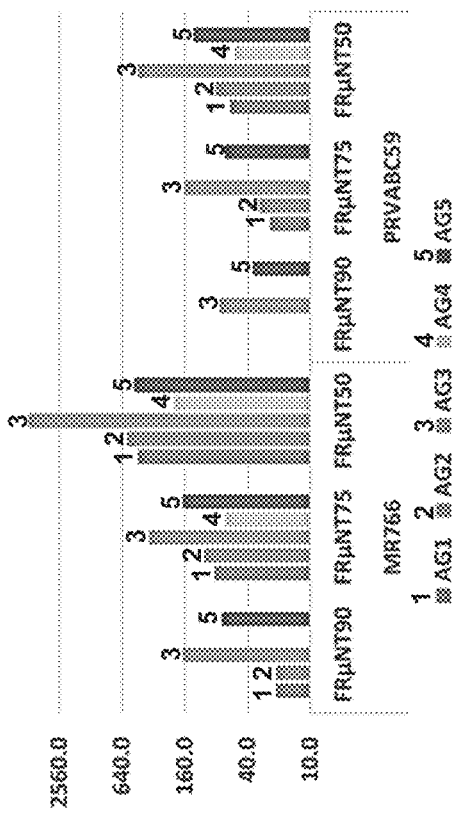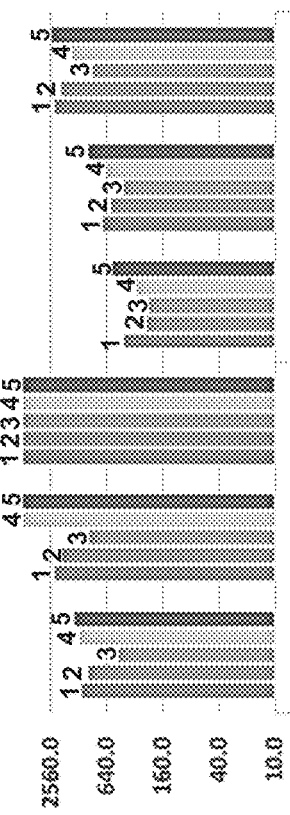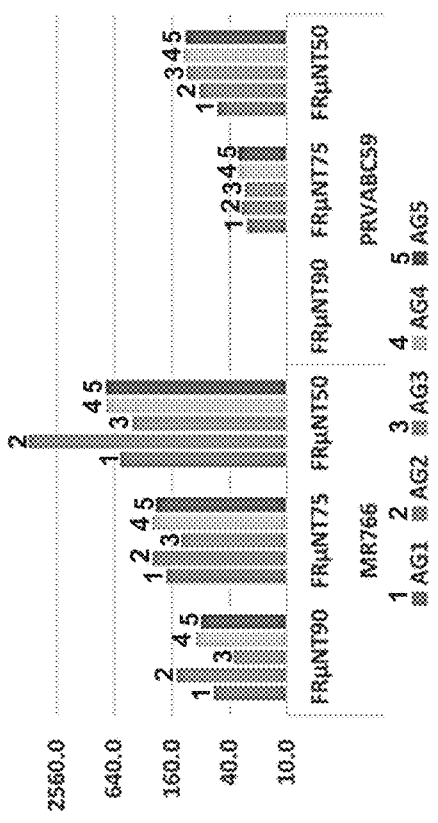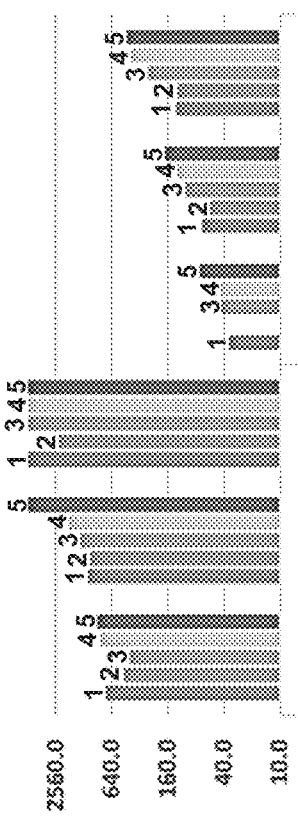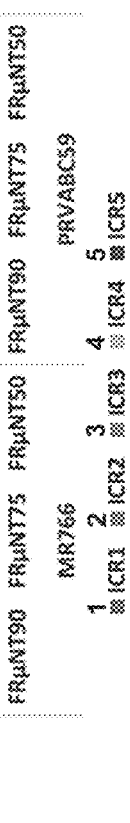
FIG. 3A  FIG. 3B  FIG. 3C  FIG. 3D

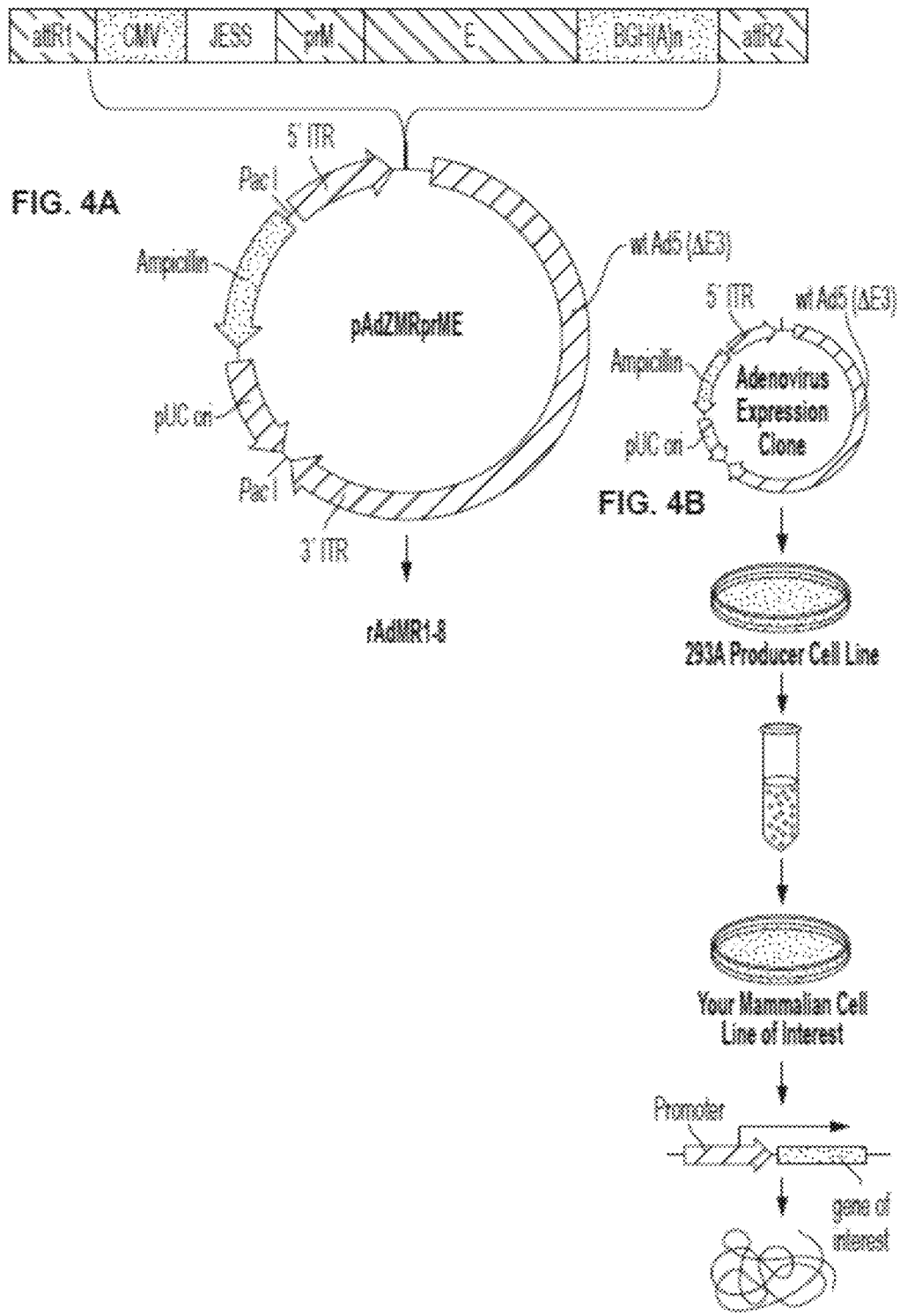

NUCLEIC ACIDS ENCODING ZIKA VIRUS-LIKE PARTICLES AND THEIR USE IN ZIKA VIRUS VACCINES AND DIAGNOSTIC ASSAYS

CROSS REFERENCE TO RELATED APPLICATIONS

This application is a divisional of U.S. patent application Ser. No. 16/309,288, filed Dec. 12, 2018, issued as U.S. Pat. No. 10,947,277 on Mar. 16, 2021, which is the U.S. National Stage of International Application No. PCT/US2017/036762, filed Jun. 9, 2017, published in English under PCT Article 21(2), which claims the benefit of U.S. Provisional Application No. 62/349,537, filed Jun. 13, 2016. The above listed applications are herein incorporated by reference in their entirety.

FIELD

This disclosure concerns Zika virus (ZIKV) transcriptional units encoding ZIKV premembrane (prM) and envelope (E) proteins (prME) and their use in ZIKV vaccine platforms and ZIKV diagnostic assays.

BACKGROUND

The twentieth and twenty-first centuries have demonstrated the benefits and risks of living in a globalized world. A microcosm of those risks is the repeat introduction and expansion of vector-borne viruses within the Flavivirus genus (such as dengue virus, West Nile virus, and Zika virus) across the world and their emergence as global public health concerns (Musso and Gubler, *Clin Microbiol Rev* 29, 487-524, 2016). The explosive expansion of an Asian genotype of Zika virus (ZIKV) across the Pacific Islands in 2013-2014, which by May of 2015 emerged in Brazil, underscores this reality (Haddow et al., *PLoS Negl Trop Dis* 6, e1477, 2012; Duffy et al., *N Engl J Med* 360, 2536-2543, 2009; Nishiura et al., *Int J Infect Dis* 45, 95-97, 2016). Since then, the Centers for Disease Control and Prevention (CDC) has established a causal link between prenatal exposure to ZIKV and an increased risk for congenital birth abnormalities, including the much publicized increased incidence of neonatal microcephaly (Driggers et al., *N Engl J Med* Epub Mar. 30, 2016; Petersen et al., *MMWR Morb Mortal Wkly Rep* 65, 30-33, 2016; Karwowski et al., *Pediatrics* Epub Mar. 23, 2016; Petersen et al., *N Engl J Med* 374, 1552-1563, 2016). Additionally, there is mounting evidence of a link between ZIKV exposure and Guillian-Barré syndrome (Cao-Lormeau et al., *Lancet* 387, 1531-1539, 2016), encephalitis (Carteaux et al., *N Engl J Med* 374, 1595-1596, 2016), and myelopathy (Mecharles et al., *Lancet* 387, 1481, 2016) in adults. Because of the global risks, particularly the risk posed to the populations of the Americas, the World Health Organization (WHO) has declared the epidemics as a Public Health Emergency of International Concern, and launched a global Strategic Response Framework and Joint Operations Plan in order to mitigate the spread and impact of the virus (Maurice, *Lancet* 387, 1147, 2016). However, with a very short window of viremic phase in humans, Zika virus provides a unique challenge to using ZIKV-specific nucleic acid based diagnostic procedures (Bingham et al., *MMWR Morb Mortal Wkly Rep* 65, 475-478, 2016), and control measures focus primarily on vector control. Thus, in order to comprehensively address the threat of ZIKV, an improved serodiagnostic assay must be developed and an effective vaccine must be made available.

ZIKV contains a single, positive sense viral RNA of 10.7 kb in-length that translates into a single poly-protein, which is subsequently cleaved into three structural proteins (capsid, premembrane/membrane, envelope; C, prM/M, E) and seven non-structural proteins (NS1, NS2A, NS2B, NS3, NS4A, NS4B, and NS5) (Kuno and Chang, *Arch Virol* 152, 687-696, 2007). It has been previously demonstrated with other flaviviruses that expression of prM and E glycoproteins alone can self-assemble and be secreted as immunogenic virus-like particles (VLPs) (Chang et al., *J Virol* 74, 4244-4252, 2000; Davis et al., *J Virol* 75, 4040-4047, 2001; Chang et al., *Virology* 306, 170-180, 2003; Konishi et al., *J Virol* 72, 4925-4930, 1998; Konishi et al., *Vaccine* 21, 3713-3720, 2003).

SUMMARY

Disclosed herein are transcriptional units encoding ZIKV prM and E proteins, which upon translation, form ZIKA VLPs. The disclosed transcriptional units and VLPs are used in a variety of ZIKV vaccine platforms, as well as in detection methods for the diagnosis of ZIKV infection.

Provided herein are isolated nucleic acid molecules including a transcriptional unit. The transcriptional unit includes a sequence encoding a modified Japanese encephalitis virus (JEV) signal sequence and a ZIKV prM and E protein (prME) coding sequence. In some embodiments, the nucleic acid molecules further include a promoter operably linked to the prME coding sequence; a transcription termination sequence; and/or a translation initiation sequence. In some examples, the prME coding sequence is codon-optimized for expression in human cells.

Further provided herein are vectors that include the disclosed nucleic acid molecules. In some embodiments, the vector is an adenovirus vector. Recombinant adenoviruses that include a nucleic acid molecule disclosed herein are also provided. The recombinant adenoviruses express ZIKV VLPs. Also provided are isolated cells that include a nucleic acid or vector disclosed herein.

Further provided herein are VLPs encoded by the nucleic acid molecules and vectors disclosed herein. In some embodiments, the VLPs include at least one amino acid substitution that reduces flavivirus cross-reactive immune responses.

Compositions, such as immunogenic compositions, that include the nucleic acid molecules, vectors, recombinant adenoviruses or VLPs disclosed herein are also provided by the present disclosure. Further provided herein are methods of eliciting an immune response against Zika virus in a subject by administering a disclosed nucleic acid molecule, vector, recombinant adenovirus, VLP or composition.

Also provided herein are methods of detecting ZIKV-specific antibodies in a biological sample. In some embodiments, the method includes contacting the sample with a ZIKV VLP disclosed herein under conditions sufficient to form VLP-antibody complexes if ZIKV antibodies are present in the sample; and detecting the VLP-antibody complexes in the sample. In other embodiments, the method includes providing a secondary antibody bound to a solid support; contacting the secondary antibody-bound solid support with the biological sample under conditions sufficient to allow binding of the secondary antibody to any ZIKV-specific antibodies present in the biological sample, thereby forming antibody-antibody complexes; contacting the antibody-antibody complexes with a ZIKV VLP disclosed herein under conditions sufficient for the VLP to bind the ZIKV-specific antibodies, thereby forming immune complexes; and detecting the presence of the immune complexes. In yet other embodiments, the method includes providing a ZIKV-specific antibody bound to a solid support; contacting the antibody-bound solid support with a ZIKV VLP disclosed herein under conditions sufficient for the VLP to bind the ZIKV-specific antibody to form antibody-VLP complexes; contacting the antibody-VLP complexes with the biological sample to allow binding of any ZIKV-specific antibodies present in the sample to the VLP, thereby forming immune complexes; contacting the immune complexes with a secondary antibody; and detecting binding of the secondary antibody to the immune complexes.

The foregoing and other objects, features, and advantages of the invention will become more apparent from the following detailed description, which proceeds with reference to the accompanying figures.

BRIEF DESCRIPTION OF THE DRAWINGS

(FIG. 1A) Schematic representation of plasmid vector pEZMRprME1-8. This plasmid includes the cytomegalovirus (CMV) promoter/enhancer element, the modified Japanese encephalitis virus (JEV) signal sequence (SS), bovine growth hormone (BGH) poly(A) signal and transcription termination sequence [BGH(A)n], kanamycin resistance gene (KanR), and pUC origin (ori) for selection and maintenance in E. coli. (FIG. 1B) Immunofluorescence analysis of prM and E protein expression in COS-1 cells transfected with the plasmids pEZMRprME1-8, pEBZHu8 (expressing human codon-optimized, synthetic prME gene of the BPH2015 strain) and pEBZHu2-3 (pr1Ala deletion clone derived from pEBZHu8). After fixation, prM/M and/or E proteins were detected with anti-ZIKV mouse hyper-immune ascetic fluid (MHIAF) or flavivirus group-cross reactive murine monoclonal antibody 4G2 (MAb 4G2), followed by incubation with goat anti-mouse IgG-FITC and Evan's blue to counterstain the cells. Fluorescence in cells indicated positive intracellular expression of prM and/or E proteins. (FIG. 1C) Detection and quantification of secreted MR766-VLPs in culture supernatants harvested from transiently transformed COS-1 cells by antigen (Ag)-capture ELISA using 4G2 and a ZIKV-specific human polyclonal serum (αZHS) as the detector antibodies. Culture supernatants were harvested on day 5 (VLP1) and day 10 (VLP2, second harvest) and concentrated 40-fold. Data points are presented as means of two independent assays. (FIG. 1D) Characterization of ZIKV VLPs and virions by Western blot analysis. The forth and eight lanes contain pre-stained protein standards. Bands corresponding to E and prM proteins are labeled on the left side of the panel. Reactivity of pelleted VLPs expressed by pEZMRprME1-8 (1-8), pEBZHu2-3 (2-3) and purified MR766 virion particles (V) with αZHS and 4G2 was tested. E and prM bands were detected by αZHS, while only E bands were detected by 4G2 in purified virions, 1-8 and 2-3 VLPs. Capsid and processed pr and M proteins were not detected by this αZHS.

FIGS. 3A-3D: ZIKV-specific neutralizing (Nt) antibody against MR766 and PRVABC59 virus in AG129 and ICR mice immunized with $10^6$ TU of rAdMR1-8 vaccine. Only AG129 mice were challenged with $10^3$ ffu of PRVABC59 virus at four weeks post vaccination. For FIGS. 3A and 3B, bars are from left to right: AG1, AG2, AG3, AG4 and AG5. For FIGS. 3C and 3D, bars are from left to right: ICR1, ICR2, ICR3, ICR4 and ICR5.

FIGS. 4A-4D: Generation of a non-infectious recombinant adenovirus vaccine (rAdMR1-8) expressing ZIKV virus-like particles. (FIG. 4A) The transcription unit expressing prM and E protein was transferred to pAdMR1-8 plasmid by homologous recombination. (FIG. 4B) Schematic representation of the procedure to generate rAdMR1-8 in 293A cells. (FIG. 4C) rAdMR1-8 is used to transduce Vero cells and its titer is measured by an antigen focus assay. (FIG. 4D) Cells expressing ZIKV VLP are counted to determine the transduction unit titer of rAdMR1-8.

SEQUENCE LISTING

Figure 1A:
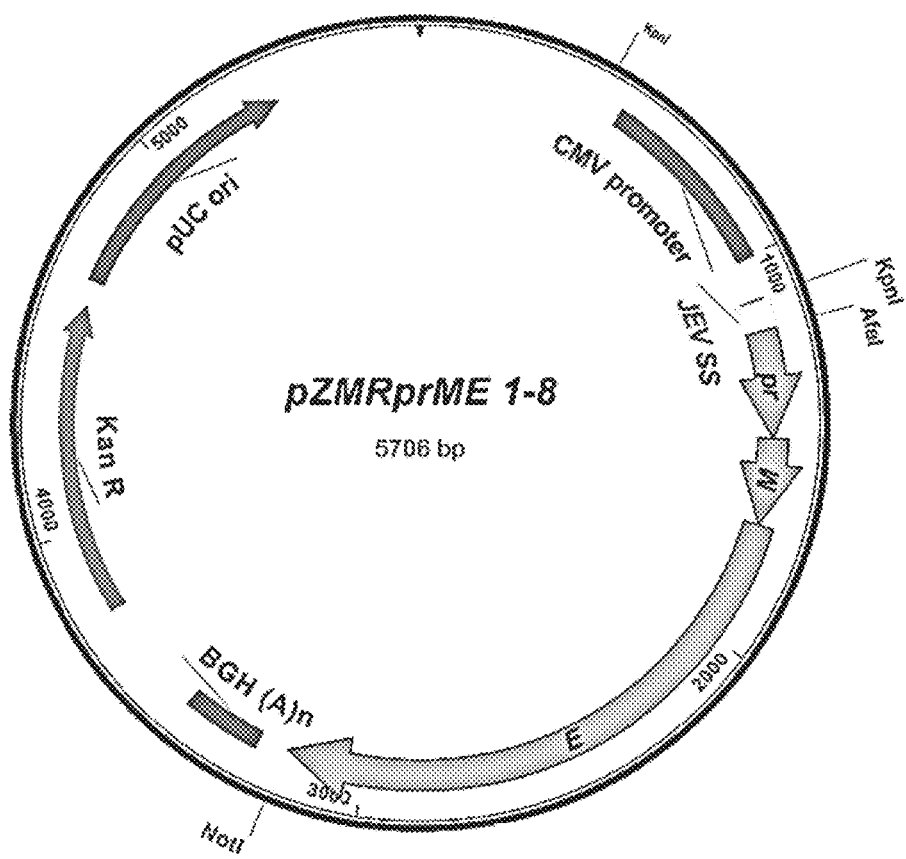
FIGS. 1A-1D: Characterization of virus-like particle (VLP) expressed prM and E proteins of ZIKV MR766 strain.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jan. 27, 2021, 71.8 KB, which is incorporated by reference herein. In the accompanying sequence listing:

SEQ ID NO: 1 is the nucleotide sequence of plasmid pEZMRprME1-8 having the following features:
  Nucleotides 517-999—CMV promoter
  Nucleotides 1105-1117—Kozak consensus sequence
  Nucleotides 1114-1185—coding sequence for modified JEV signal sequence
  Nucleotides 1186-3204—prME coding sequence
  Nucleotides 3279-3479—BGH) poly(A) signal and transcription termination sequence.

SEQ ID NO: 2 is the nucleotide sequence of plasmid pEBZHu8, having the following features:
  Nucleotides 517-999—CMV promoter
  Nucleotides 1105-1117—Kozak consensus sequence Nucleotides 1114-1185—coding sequence for modified JEV signal sequence Nucleotides 1186-3213—prME coding sequence Nucleotides 3288-3488—BGH poly(A) signal and transcription termination sequence.

SEQ ID NO: 3 is the nucleotide sequence of plasmid pEBZHu2-3, having the following features:

Nucleotides 517-999—CMV promoter

Nucleotides 1105-1117—Kozak consensus sequence

Nucleotides 1114-1185—coding sequence for modified JEV signal sequence

Nucleotides 1186-3210—prME coding sequence

Nucleotides 3285-3485—BGH) poly(A) signal and transcription termination sequence.

SEQ ID NO: 4 is the amino acid sequence of a modified JEV signal sequence.

SEQ ID NO: 5 is the amino acid sequence of prME expressed by plasmid pEZMRprME1-8, having the following features:

Residues 1-93—pr sequence

Residues 94-168—M protein

Residues 169-672—E protein.

SEQ ID NO: 6 is the amino acid sequence of prME expressed by plasmid pEBZHu8, having the following features:

Residues 1-94 pr sequence

Residues 95-169—M protein

Residues 170-675—E protein.

SEQ ID NO: 7 is the amino acid sequence of prME expressed by plasmid pEBZHu2-3, having the following features:

Residues 1-93 pr sequence

Residues 94-168—M protein

Residues 169-674—E protein.

SEQ ID NO: 8 is the nucleotide sequence of a Kozak consensus sequence.

SEQ ID NOs: 9-19 are amino acid sequences containing furin and signalase cleavage sites (see Table 1).

SEQ ID NO: 20 is the nucleotide sequence of plasmid pEZMRprME KD having the following features:

Nucleotides 517-999—CMV promoter

Nucleotides 1105-1117—Kozak consensus sequence

Nucleotides 1114-1185—coding sequence for modified JEV signal sequence

Nucleotides 1186-3204—prME coding sequence with modifications at E106/107

Nucleotides 3279-3479—BGH) poly(A) signal and transcription termination sequence.

SEQ ID NO: 21 is the amino acid sequence of prME expressed by plasmid pEZMRprME KD, having the following features:

Residues 1-93—pr sequence

Residues 94-168—M protein

Residues 169-672—E protein with K/K at residues 274/275.

SEQ ID NO: 22 is the nucleotide sequence of plasmid pEBZHu2-3 KD, having the following features:

Nucleotides 517-999—CMV promoter

Nucleotides 1105-1117—Kozak consensus sequence

Nucleotides 1114-1185—coding sequence for modified JEV signal sequence

Nucleotides 1186-3210—prME coding sequence with modifications at E106/107

Nucleotides 3285-3485—BGH) poly(A) signal and transcription termination sequence.

SEQ ID NO: 23 is the amino acid sequence of prME expressed by plasmid pEBZHu2-3 KD, having the following features:

Residues 1-93 pr sequence

Residues 94-168—M protein

Residues 169-674—E protein with K/D at residues 274/275.

SEQ ID NOs: 24-29 are primer sequences.

DETAILED DESCRIPTION

I. Abbreviations

Ad adenovirus
Ag antigen
BGH bovine growth hormone
CMV cytomegalovirus
E envelope (protein)
ELISA enzyme-linked immunosorbent assay
IFA immunofluorescent antibody assay or immunofluorescence assay
i.m. intramuscularly
i.p. intraperitoneally
ffu focus forming unit
FRpNT focus-reduction micro-neutralization test
GAC-ELISA IgG antibody-captured ELISA
GBS Guillan-Barré syndrome
JESS Japanese encephalitis signal sequence
JEV Japanese encephalitis virus
M membrane (protein)
MAb monoclonal antibody
MHIAF mouse hyper-immune ascetic fluid
NS non-structural (protein)
Nt neutralizing
OD optical density
PC post challenge
pfu plaque forming unit
prM premembrane (protein)
PV post vaccination
RT-PCR reverse transcriptase polymerase chain reaction
SS signal sequence
TU transduction unit
VLP virus-like particle
WHO World Health Organization
ZIKV Zika virus

II. Terms and Methods

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adenovirus (Ad): A non-enveloped virus with a liner, double-stranded DNA genome and an icosahedral capsid. There are at least 68 known serotypes of human adenovirus, which are divided into seven species (species A, B, C, D, E, F and G). Different serotypes of adenovirus are associated with different types of disease, with some serotypes causing respiratory disease (primarily species B and C), conjunctivitis (species B and D) and/or gastroenteritis (species F and G). Modified adenoviruses are often used for delivery of exogenous DNA, such as for vaccination or gene therapy.

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition (e.g. an immunogenic composition) to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Biological sample: A sample obtained from a subject (such as a human or veterinary subject). Biological samples, include, for example, fluid, cell and/or tissue samples. In some embodiments herein, the biological sample is a fluid sample. Fluid sample include, but are not limited to, serum, blood, plasma, urine, feces, saliva, cerebral spinal fluid (CSF) and bronchoalveolar lavage (BAL) fluid.

Capsid protein (C protein): One of three flavivirus structural proteins that forms the flavivirus particle. The C protein is a dimeric, alpha-helical protein with an unstructured N-terminus. In flavivirus particles, the C protein is found internal to the lipid bilayer and directly contacts the flavivirus genomic RNA.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammals, or more specifically, humans. Codon optimization does not alter the amino acid sequence of the encoded protein.

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule (such as an antibody) with a biological sample.

Control: A reference standard, for example a positive control or negative control. A positive control is known to provide a positive test result. A negative control is known to provide a negative test result. However, the reference standard can be a theoretical or computed result, for example a result obtained in a population.

Detectable label: A detectable compound or composition that is conjugated directly or indirectly to another molecule, such as an antibody, protein or microparticle, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Envelope (E) glycoprotein: A flavivirus (including Zika virus) structural protein that mediates binding of flavivirus virions to cellular receptors on host cells. The flavivirus E protein is required for membrane fusion, and is the primary antigen inducing protective immunity to flavivirus infection. Flavivirus E protein affects host range, tissue tropism and viral virulence. The flavivirus E protein contains three structural and functional domains, DI-DIII. In mature virus particles the E protein forms head to tail homodimers lying flat and forming a dense lattice on the viral surface. As used herein, "positions 106 and 107" or "residues 106 and 107" of the ZIKV E protein refer to the amino acids corresponding to residues 274 and 275 of the prME amino acid sequences set forth herein as SEQ ID NO: 21 and SEQ ID NO: 23.

Fluorophore: A chemical compound, which when excited by exposure to a particular wavelength of light, emits light (i.e., fluoresces), for example at a different wavelength.

Examples of fluorophores that may be used in the compositions and methods disclosed herein are provided in U.S. Pat. No. 5,866,366 to Nazarenko et al.: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; R-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N', N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999).

Other suitable fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art may also be used.

Heterologous: A heterologous protein or polypeptide refers to a protein or polypeptide derived from a different source or species.

Immune complex: A protein complex that comprises an antibody bound to an antigen. In the context of the present disclosure, the term "immune complex" is used to indicate a protein complex that includes an antigen (such as a VLP) bound to at least one antibody. In some cases, the immune complex includes an antigen (such as a VLP) bound to two separate antigen-specific antibodies (each binding a different epitope of the antigen), or includes an antigen (such as a VLP) bound to an antigen-specific antibody, which is further bound to a secondary antibody. The term "antibody-antigen complex" or "antibody-VLP complex" is used to refer to an antigen (or VLP) bound to one antibody. Furthermore, the term "antibody-antibody complex" is used to refer to an antibody bound to a different antibody (such as an antigen-specific antibody bound to a secondary antibody).

Immune response: A response of a cell of the immune system, such as a B-cell, T-cell, macrophage or polymorphonucleocyte, to a stimulus such as an antigenic polypeptide or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunize: To render a subject protected from an infectious disease, such as by vaccination.

Isolated: An "isolated" or "purified" biological component (such as a nucleic acid, peptide, protein, protein complex, or virus-like particle) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compositions, such as one or more Zika virus vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate.

In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

A conservative substitution in a polypeptide is substitution of one amino acid residue in a protein sequence for a different amino acid residue having similar biochemical properties. Typically, conservative substitutions have little to no impact on the activity of a resulting polypeptide. For example, a flavivirus protein including one or more conservative substitutions (for example no more than 2, 5, 10, 20, 30, 40, or 50 substitutions) retains the structure and function of the wild-type protein. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Premembrane (prM) protein: A flavivirus structural protein. The prM protein is an approximately 25 kDa protein that is the intracellular precursor for the membrane (M) protein. prM is believed to stabilize the E protein during transport of the immature virion to the cell surface. When the virus exits the infected cell, the prM protein is cleaved to the mature M protein, which is part of the viral envelope (Reviewed in Lindenbach and Rice, In: *Fields Virology*, Knipe and Howley, eds., Lippincott, Williams, and Wilkins, 991-1041, 2001).

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of one or more signs or symptoms of a disease.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some embodiments herein, the promoter is a cytomegalovirus (CMV) promoter, such as the CMV E1A promoter.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids, proteins and viruses that have been altered solely by addition, substitution, or deletion of a portion of a natural nucleic acid molecule, protein or virus.

Secondary antibody: An antibody that specifically recognizes the Fc region of a particular isotype of antibody (for example specifically recognizes human IgG or human IgM). Secondary antibodies for use with the methods disclosed herein include, but are not limited to, anti-human IgG and anti-human IgM. In some embodiments herein, the secondary antibody is conjugated to a detectable label, such as a fluorophore, enzyme or radioisotope, to facilitate detection of antibodies and/or immune complexes to which the secondary antibody is bound.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Serum: The fluid portion of the blood that separates out from clotted blood. Serum contains many proteins, including antibodies, but does not contain clotting factors.

Signal sequence: A short amino acid sequence found at the N-terminus of most newly synthesized proteins that are targeted to the secretory pathway. In some embodiments herein, the signal sequence is a JEV signal sequence, such as the JEV signal sequence present at the N-terminus of the prM protein. In particular examples, the signal sequence is a modified JEV prM signal sequence having the amino acid sequence of SEQ ID NO: 4.

Subject: Living multi-cellular vertebrate organisms, a category that includes both human and non-human mammals (such as mice, rats, rabbits, sheep, horses, cows, and non-human primates).

Therapeutically effective amount: A quantity of a specified agent (such as an immunogenic composition) sufficient to achieve a desired effect in a subject being treated with that agent. For example, this may be the amount of a virus vaccine useful for eliciting an immune response in a subject and/or for preventing infection by the virus. In the context of the present disclosure, a therapeutically effective amount of a Zika virus vaccine, for example, is an amount sufficient to increase resistance to, prevent, ameliorate, and/or treat infection caused by Zika virus in a subject without causing a substantial cytotoxic effect in the subject. The effective amount of a Zika virus vaccine (or Zika virus immunogenic composition) useful for increasing resistance to, preventing, ameliorating, and/or treating infection in a subject will be dependent on, for example, the subject being treated, the manner of administration of the therapeutic composition and other factors.

Transcriptional unit: A nucleic acid that codes for a single RNA molecule and includes the sequences necessary for transcription of the encoded RNA.

Transcription termination sequence: A nucleic acid sequence that marks the end of a gene or operon during transcription. A transcription termination sequence mediates termination of transcription by providing signals in the newly synthesized RNA that trigger processes that release the mRNA from the transcriptional complex. In some embodiments herein, the transcription termination sequence is a BGH transcription termination sequences, such as the sequence set forth as nucleotides 3279-3479 of SEQ ID NO: 1.

Translation initiation sequence: A nucleic acid sequence that mediates the initiation of translation of an RNA. In some embodiments herein, the translation initiation sequence is a Kozak consensus sequence comprising SEQ ID NO: 8.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins (including VLPs), peptides or DNA derived from them. An attenuated vaccine is a virulent organism that has been modified to produce a less virulent form, but nevertheless retains the ability to elicit antibodies and cell-mediated immunity against the virulent form. A killed vaccine is a previously virulent microorganism that has been killed with chemicals or heat, but elicits antibodies against the virulent microorganism. Vaccines may elicit both prophylactic (preventative) and therapeutic responses. Methods of administration vary according to the vaccine, but may include inoculation, ingestion, inhalation or other forms of administration. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes.

Virus-like particle (VLP): Virus particles made up of one of more viral structural proteins, but lacking the viral genome. Because VLPs lack a viral genome, they are non-infectious. In some embodiments, the VLPs are flavivirus VLPs, such as Zika virus VLPs. In particular examples, flavivirus VLPs include two flavivirus structural proteins—prM/M and E.

Zika virus (ZIKV): A member of the virus family Flaviviridae and the genus Flavivirus. Other members of this genus include dengue virus, yellow fever virus, Japanese encephalitis virus (JEV), West Nile virus and Spondweni virus. ZIKV is spread by the daytime-active mosquitoes *Aedes aegypti* and *A. albopictus*. This virus was first isolated from a Rhesus macaque from the Zika Forest of Uganda in 1947. Since the 1950s, ZIKV has been known to occur within a narrow equatorial belt from Africa to Asia. The virus spread eastward across the Pacific Ocean in 2013-2014, resulting in ZIKV outbreaks in Oceania to French Polynesia, New Caledonia, the Cook Islands, and Easter Island. In 2015, ZIKV spread to Mexico, Central America, the Caribbean and South America, where ZIKV has reached pandemic levels. Infection by ZIKV generally causes either no symptoms are mild symptoms, including mild headache, maculopapular rash, fever, malaise, conjunctivitis and joint pain. ZIKV causes symptoms in about 20% of infected individuals, and no deaths from the virus have yet been reported. However, ZIKV infection has been linked to the birth of microcephalic infants following maternal infection, as well an increase in cases of GBS. Reports have also indicated that ZIKV has the potential for human blood-borne and sexual transmission. ZIKV has also been found in human saliva and breastmilk. There are currently no available medical countermeasures for the treatment or prevention of Zika virus infection (Malone et al., *PLoS Negl Trop Dis* 10(3):e0004530, 2016).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

To address the public health emergency that has arisen from the rapid spread of ZIKV, the present disclosure provides compositions for use as ZIKV vaccines, as well as reagents and methods for detection of ZIKV infection in susceptible individuals. In particular, disclosed herein are transcriptional units that encode ZIKV prM and E proteins (prME), which upon expression, form virus-like particles (VLPs). In specific embodiments, the transcriptional units encode a modified Japanese encephalitis virus (JEV) prM signal sequence to improve protein translocation and VLP secretion. In some examples, the transcriptional units also include a CMV promoter/enhancer element to improve mRNA synthesis, a Kozak translation initiation sequence to enhance translation, and a bovine growth hormone (BGH) poly(A) signal and transcription termination sequence. Three prME expression plasmids derived from three different ZIKV strains (MR766, P6-740 and BPH2015) were generated. MR766 is the prototype African genotype virus; P6-740 is the prototype Asian genotype virus; and BPH2015 is the current circulating Asian genotype virus. Also disclosed are two mutant constructs based on MR766 and BHP2015 that express VLPs having amino acid substitutions at positions 106 and 107 of the E protein.

The ZIKV transcriptional units were used in the development of three different vaccine platforms—a plasmid DNA vaccine that includes the transcriptional unit; a recombinant adenovirus (rAd) harboring the transcriptional unit (and that expresses ZIKV VLPs upon transduction of a cell); and VLPs isolated from cells expressing the transcriptional unit.

Though previous flavivirus vaccine work has focused on using a plasmid DNA based vaccine, there is evidence to suggest that a non-replicating vector-based protein nanoparticle (Ledgerwood et al., *Vaccine* 29, 304-313, 2010; Smaill et al., *Sci Transl Med* 5(205):205ra134, 2013; Zhu et al., *Lancet* 385, 2272-2279, 2015) would be an efficient platform to deliver a transcription, translation and protein processing optimized vaccine component, thereby producing a ZIKV vaccine capable of eliciting a strong immune response. Thus, in one aspect, disclosed herein is the construction of a ZIKV prME transcriptional unit and insertion of the optimized transcriptional unit into a non-infectious rAd serotype 5 vector. The rAd ZIKV vaccine was tested for efficacy as a single-dose vaccine and shown to provide protective immunity in a mouse challenge model.

In addition, methods of using ZIKV VLPs encoded by the transcriptional units to develop immunoassays, such as antibody capture ELISAs, to enable detection of anti-ZIKV antibodies from patient samples is also described.

IV. Overview of Several Embodiments

Disclosed herein are transcriptional units encoding ZIKV prM and E proteins, which upon translation, form ZIKA VLPs. The disclosed transcriptional units and VLPs are suitable for use with a variety of ZIKV vaccine platforms, as well as in multiple different detection methods for the diagnosis of ZIKV infection.

Provided herein are isolated nucleic acid molecules that include a ZIKV transcriptional unit. In some embodiments, the transcriptional units include a sequence encoding a modified Japanese encephalitis virus (JEV) signal sequence, and include a ZIKV prME coding sequence. In some examples, the modified JEV signal sequence comprises SEQ ID NO: 4, or comprises no more than 5, no more than 4, no more than 3, no more than 2 or no more than 1 substitution(s) relative to SEQ ID NO: 4.

In some embodiments, the transcriptional unit further includes a promoter operably linked to the prME coding sequence. In some examples, the promoter is a CMV promoter, such as the CMV E1A promoter. In specific examples, the promoter sequence is at least 80%, at least 85%, at least 90%, at least 95%, at least 96%, at least 97%, at least 98% or at least 99% identical to nucleotides 517-999 of SEQ ID NO: 1. In one non-limiting example, the promoter sequence comprises or consist of nucleotides 517-999 of SEQ ID NO: 1.

In some embodiments, the transcriptional unit further includes a transcription termination sequence. In some examples, the transcription termination sequence comprises a bovine growth hormone (BGH) transcription termination sequence. In specific examples, the transcription termination sequence is at least 80%, at least 85%, at least 90%, at least 95%, at least 96%, at least 97%, at least 98% or at least 99% identical to nucleotides 3279-3479 of SEQ ID NO: 1. In one non-limiting example, the transcription termination sequence comprises or consists of nucleotides 3279-3479 of SEQ ID NO: 1.

In some embodiments, the transcriptional unit further includes a translation initiation sequence. In some examples, the translation initiation sequence is a Kozak consensus sequences, such as the sequence GCCGCCGCCATGG (SEQ ID NO: 8).

In some embodiments, the ZIKV is an African genotype strain, such as MR-766. In other embodiments, the ZIKV is an Asian genotype strain, such as SPH2015, P6-740, or FSS 13025.

In some embodiments, the prME coding sequence is codon-optimized for expression in human cells.

In some embodiments, the ZIKV prME coding sequence is at least 80%, at least 85%, at least 90%, at least 95%, at least 96%, at least 97%, at least 98% or at least 99% identical to nucleotides 1186-3204 of SEQ ID NO: 1, nucleotides 1186-3213 of SEQ ID NO: 2, nucleotides 1186-3210 of SEQ ID NO: 3, nucleotides 1186-3204 of SEQ ID NO: 20 or nucleotides 1186-3210 of SEQ ID NO: 22. In some examples, the ZIKV prME coding sequence comprises or consists of nucleotides 1186-3204 of SEQ ID NO: 1, nucleotides 1186-3213 of SEQ ID NO: 2, nucleotides 1186-3210 of SEQ ID NO: 3, nucleotides 1186-3204 of SEQ ID NO: 20 or nucleotides 1186-3210 of SEQ ID NO: 22.

Also provided herein is a vector that includes a nucleic acid molecule (a transcriptional unit) disclosed herein. In some embodiments, the vector is a plasmid vector. In other embodiments, the vector is an adenovirus vector. In some examples, the vector is a replication-incompetent adenovirus vector.

Further provided are isolated cells that contain a nucleic acid molecule (transcriptional unit) or vector disclosed herein.

Recombinant adenoviruses that include a nucleic acid molecule disclosed herein are also provided. By harboring the transcriptional unit, the recombinant adenoviruses express ZIKV VLPs upon transduction of a host cell.

Also provided herein are VLPs encoded by a nucleic acid molecule (or vector) disclosed herein. In some embodiments, the E protein of the VLP includes at least one amino acid substitution that reduces cross-reactivity. In some examples, the at least one amino acid substitution is at position 106 and/or position 107 of the E protein (corresponding to residues 274 and 275 of the prME sequences set forth herein as SEQ ID NO: 21 and SEQ ID NO: 23). In specific examples, the E protein of the VLP has a lysine at position 106 and an aspartic acid at position 107; an arginine at position 106 and an aspartic acid at position 107; an arginine at position 106 and a histidine at position 107; a glutamic acid at position 106 and an aspartic acid at position 107; or a glutamic acid at position 106 and an arginine at position 107. In particular non-limiting examples, the prME amino acid sequence of the VLP comprises SEQ ID NO: 21 or SEQ ID NO: 23.

Compositions, such as immunogenic compositions, that include a nucleic acid molecule, vector, recombinant adenovirus or VLP disclosed herein, and a pharmaceutically acceptable carrier, are further provided herein.

Also provided herein are methods of eliciting an immune response against ZIKV in a subject by administering to the subject a nucleic acid molecule, vector, recombinant adenovirus, VLP or composition disclosed herein. In some embodiments, the subject is a human. The immune response may include, for example, induction of ZIKV-specific antibodies (such as IgM and/or IgG antibodies) or induction of a virus-specific T cell response. In some examples, the immune response is a protective immune response.

Further provided is a method of immunizing a subject against ZIKV by administering to the subject a nucleic acid molecule, vector, recombinant adenovirus, VLP or composition disclosed herein. In some embodiments, the subject is a human.

Also provided herein are methods of detecting ZIKV-specific antibodies in a biological sample. In some embodiments, the method includes contacting the sample with a ZIKV VLP disclosed herein under conditions sufficient to form VLP-antibody complexes if ZIKV antibodies are present in the sample; and detecting the VLP-antibody complexes in the sample. In some examples, detecting the VLP-antibody complexes includes contacting the VLP-antibody complexes with an antibody that specifically binds the VLP and comprises a detectable label. In other examples, detecting the VLP-antibody complexes comprises contacting the VLP-antibody complexes with a secondary antibody comprising a detectable label. In specific examples, the secondary antibody is an anti-IgM antibody or an anti-IgG, such as anti-human IgM antibody or an anti-human IgG antibody.

In other embodiments, the method includes providing a secondary antibody bound to a solid support; contacting the secondary antibody-bound solid support with the biological sample under conditions sufficient to allow binding of the secondary antibody to any ZIKV-specific antibodies present in the biological sample, thereby forming antibody-antibody complexes; contacting the antibody-antibody complexes with a ZIKV VLP disclosed herein under conditions sufficient for the VLP to bind the ZIKV-specific antibodies, thereby forming immune complexes; and detecting the presence of the immune complexes. In some examples, detecting the presence of the immune complexes includes contacting the immune complexes with an antibody that specifically binds the VLP and comprises a detectable label. In some examples, the secondary antibody is an anti-IgM antibody, such as anti-human IgM antibody. In other examples, the secondary antibody is an anti-IgG antibody, such as anti-human IgG antibody.

In yet other embodiments, the method includes providing a ZIKV-specific antibody bound to a solid support; contacting the antibody-bound solid support with a ZIKV VLP disclosed herein under conditions sufficient for the VLP to bind the ZIKV-specific antibody to form antibody-VLP complexes; contacting the antibody-VLP complexes with the biological sample to allow binding of any ZIKV-specific antibodies present in the sample to the VLP, thereby forming immune complexes; contacting the immune complexes with a secondary antibody; and detecting binding of the secondary antibody to the immune complexes. In some examples, the secondary antibody is an anti-IgM antibody, such as anti-human IgM antibody. In other examples, the secondary antibody is an anti-IgG antibody, such as anti-human IgG antibody.

In some embodiments of the methods of detecting ZIKV-specific antibodies, the biological sample is a biological fluid sample. In some examples, the biological fluid sample comprises serum, blood or plasma. In particular examples, the biological sample comprises serum.

V. Immunogenic Compositions and Administration Thereof

Immunogenic compositions that include a nucleic acid (such as a vector) comprising a ZIKV transcriptional unit encoding prME, a rAd comprising the transcriptional unit, or VLPs encoded by the transcriptional unit, can be administered to a subject to induce a ZIKV-specific immune response in a subject. The immunogenic compositions can be used prophylactically to prevent ZIKV infection, or therapeutically to promote a ZIKV immune response. The provided nucleic acid molecules, vectors, recombinant adenoviruses and VLPs are combined with a pharmaceutically acceptable carrier or vehicle for administration as a composition to human or animal subjects.

In embodiments in which a nucleic acid encoding prME is administered (either as part of a plasmid DNA or encoded by a recombinant adenovirus), the composition administered to a subject directs the synthesis of a ZIKV prME as described herein, and a cell within the body of the subject, after incorporating the nucleic acid within it, secretes ZIKV VLPs. VLPs then serve as an in vivo immunostimulatory composition, stimulating the immune system of the subject to generate protective immunological responses against ZIKV.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immune stimulatory compositions, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on the route of administration. By way of example, intramuscular injections may range from about 0.1 ml to about 1.0 ml. Those of ordinary skill in the art will know appropriate volumes for different routes of administration.

Immune stimulatory compounds (for example, vaccines) can be administered by directly injecting nucleic acid molecules encoding polypeptide antigens (broadly described in Janeway & Travers, *Immunobiology: The Immune System In Health and Disease*, page 13.25, Garland Publishing, Inc., New York, 1997; and McDonnell & Askari, *N. Engl. J. Med.* 334:42-45, 1996), including virus-like particles. Vectors that include nucleic acid molecules described herein, or that include a nucleic acid sequence encoding ZIKV prME may be utilized in such DNA vaccination methods.

Thus, the term "immune stimulatory composition" or "immunogenic composition" as used herein also includes nucleic acid vaccines in which a nucleic acid molecule encoding a ZIKV prME is administered to a subject in a pharmaceutical composition. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264:16985, 1989), co-precipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992; Eisenbraun et al., *DNA Cell Biol.* 12:791, 1993), and in vivo infection using cloned retroviral vectors (Seeger et al., *Proc. Natl. Acad. Sci.* 81:5849, 1984). Similarly, nucleic acid vaccine preparations can be administered via viral carrier.

The amount of antigen in each dose of an immunogenic composition is selected as an amount that induces an immunostimulatory or immunoprotective response without significant, adverse side effects. Such amount will vary depending upon several factors. Initial injections may range from about 1 μg to about 1 mg, with some embodiments having a range of about 10 g to about 800 μg, and still other embodiments a range of from about 25 μg to about 500 μg. Following an initial administration of the immune stimulatory composition, subjects may receive one or several booster administrations, adequately spaced. Booster administrations may range from about 1 μg to about 1 mg, with other embodiments having a range of about 10 μg to about 750 μg, and still others a range of about 50 μg to about 500 μg. Periodic boosters at intervals of 1-5 years, for instance three years, may be desirable to maintain the desired levels of protective immunity.

The pharmaceutical or immunogenic compositions may be administered in combination with other therapeutic treatments. For example, the compositions provided herein can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

VI. Detection of Zika Virus Antibodies in Patient Samples

Serological methods of detecting ZIKV-specific antibodies in a biological sample, such as a serum sample, are disclosed herein. These methods use the ZIKV VLPs disclosed herein. Detection assays based on binding of an antigen to an antibody are well known in the art and include, for example, ELISA, microsphere immunoassay (MIA), immunofluorescence assay (IFA), Western blot, fluorescence activated cell sorting (FACS), radioimmunoassay (RIA), immunohistochemistry (IHC) and plaque reduction neutralization test (PRNT). As is well known to one of skill in the art, in some cases the detection assay further includes the step of contacting an antigen-antibody complex with a detection reagent, such as a labeled secondary antibody (e.g., an anti-isotype antibody, such as an anti-IgG antibody), or in the case of a sandwich ELISA, a second antibody that recognizes the same antigen as the first antibody and is labeled for detection. Secondary antibodies can also be conjugated to magnetic beads to allow for magnetic sorting. In other cases, the primary antibody is directly labeled. Directly labeled antibodies can be used for a variety of detection assays, such as FACS. The ZIKV VLPs disclosed herein can be used with a variety of immune-based detection assays for the diagnosis of ZIKV infection. Several exemplary immune-based detection assays are described below.

A. IgM or IgG Antibody Capture ELISAs

The immune response following a flavivirus infection includes the production of IgM and IgG antibodies, which are primarily directed against the flavivirus E protein. IgM antibody capture (MAC) or IgG antibody capture (GAC) ELISAs are commonly used to detect the level of IgM or IgG (respectively) in serum samples of patients suspected of having a flavivirus infection. In these assays, anti-human IgM or anti-human IgG serves as a capture antibody and is coated onto an appropriate assay plate, such as a multi-well plate. After blocking of the plate, such as with nonfat dry milk, diluted human sera are reacted with the anti-human IgM or IgG. In the context of the present disclosure, purified ZIKV VLPs, which serve as the antigen, are added to the plates. A ZIKV antigen-specific antibody conjugated to detectable label (for example, an enzyme or fluorophore) is then reacted with the immobilized VLPs. The detectable label is then measured to detect the presence of ZIKV-specific antibodies that were present in the serum sample. Serial dilutions of positive sera can be evaluated. The maximum dilution that exhibits positive signal is the titer for the serum. The titer of the MAC-ELISA or GAC-ELISA can be compared with the titers of other tests, such as hemagglutination inhibition tests (HIT) or PRNT. Serum samples can also be tested on control antigen in addition to viral antigen, to reduce the number of false-positive results due to non-specific binding of the serum or other factors (U.S. Patent Application Publication No. 2006/0115896).

B. Microsphere Immunoassay (MIA)

Microsphere immunoassays are becoming increasingly popular for laboratory diagnosis of many diseases (Earley et al., *Cytometry* 50:239-242, 2002; Kellar et al., *Cytometry* 45:27-36, 2001). The technology involves the detection and analysis of a reaction (such as an antibody or other ligand) attached to microspheres or beads. The detecting instrument is a simplified flow cytometer, and lasers simultaneously identify the microsphere sets and measure the fluorescence associated with the reaction. The speed at which these tests can be performed and the ability to multiplex make this methodology particularly useful.

A MIA can be used to detect the presence of Zika virus-specific antibodies in a sample. In some embodiments, microsphere beads are coated with a ZIKV-specific antibody and contacted with a ZIKV VLP (as disclosed herein) such that the ZIKV VLPs bind to the microsphere-bound Zika virus-specific antibodies. The microsphere immune complexes are mixed with a serum sample such that antibodies in the sample that are specifically reactive with the ZIKV VLPs bind the VLPs bound (indirectly) to the microsphere. The bead-bound immune complexes are allowed to react with fluorescent-dye labeled anti-species antibody (such as PE-labeled anti-human IgM or anti-human IgG), and are measured using a microsphere reader (such as a Luminex instrument). In an alternative embodiment, microsphere beads are coated directly with the ZIKV VLPs and VLP-bound microspheres are contacted with the serum samples.

C. Indirect ELISA

Indirect ELISAs to detect the presence of virus-specific antibodies are typically carried out by coating a microtiter plate with an antigen-specific antibody (such as a ZIKV-specific antibody), blocking the plates to prevent non-specific binding to the plate surface, and adding virus antigen (such as a ZIKV VLP) to allow binding of the antigen to the virus-specific antibody. After several washes, diluted human sera is added to allow binding of any antibodies present in the sample to the immobilized viral antigens (e.g. the VLP antigens). IgM or IgG antibodies that were present in the sample are then detected using a labelled secondary antibody, such as anti-human IgG or anti-human IgM conjugated to a detectable label (such as an enzyme or fluorophore). The presence of ZIKV-specific antibody is detected by measuring the detectable label (for example, by measuring fluorescence, optical density or colorimetric absorbance).

The following examples are provided to illustrate certain particular features and/or embodiments. These examples should not be construed to limit the disclosure to the particular features or embodiments described.

EXAMPLES

Example 1: Materials and Methods

This example describes the materials and experimental procedures used for the studies described in Example 2.

Cells and Viruses

COS-1, Vero E6, 293A and C6/36 cells were grown in Dulbecco's Modified Eagle's Medium (DMEM, GIBCO®, Grand Island, N.Y., USA) with 10% heat-inactivated fetal bovine serum (FBS, Hyclone®, Logan, Utah, USA). All media were supplemented with 2 mM L-glutamine, 110 mg/L sodium pyruvate, 0.1 mM non-essential amino acids, 20 mL/L 7.5% $NaHCO_3$, 100 U/mL penicillin, and 100 μg/mL streptomycin. All cells were maintained at 37° C. with 5% $CO_2$ except for C6/36 cells, which were maintained at 28° C. without $CO_2$.

The strains of Zika virus used in this study included viruses belonging to the African genotype (Monkey/Uganda/1947/MR766) and Asian genotype (Mosq/Malaysia/1966/P6-740; Hu/Cambodia/2010/FSS 13025; and Hu/Puerto Rico/2015/PRVABC59). All viruses were obtained from the collection of Division of Vector-borne Diseases (DVBD), CDC, Fort Collins, Colo. Virus stocks were propagated by infecting Vero E6 cells in DMEM with 2% FBS for 5-7 days. Culture supernatants were harvested, clarified by centrifugation, and stored in aliquots at −80° C.

Virus Titer Determination

Virus quantification was determined by antigen focus forming test in Vero cells. Briefly, $2.475\times10^4$ Vero cells/well were seeded into flat-bottom 96-well Costar® cell culture plates (Corning Inc., Corning, N.Y.) and incubated 16 hours overnight at 37° C. with 5% $CO_2$. Viruses to be quantified were diluted at 10-fold serial dilution in BA1 medium (5% BSA in 1×DMEM) and L of the serial diluted viruses were inoculated in duplicate into plates containing a Vero cell monolayer. Plates were incubated for 1 hour at 37° C. with 5% $CO_2$ and rocked every 10 minutes to allow infection. Overlay medium containing 1% methylcellulose (Sigma-Aldrich Inc., St. Louis, Mo.) in DMEM with 2% FBS was added and plates were incubated at 37° C. with 5% $CO_2$. Forty hours later, plates were washed, fixed with 75% acetone in PBS and air-dried. Immunostaining was performed by adding anti-ZIKV MHIAF at 1:2,000 in PBS and incubating for 60 minutes at 37° C., washing and adding goat anti-mouse IgG-HRP (Jackson labs, West Grove, Pa.) at 1:100 in 5% skim milk in PBS and incubating for 45 minutes at 37° C. Infection foci were developed using peroxidase substrate kit Vector® VIP SK-4600 (Vector Laboratories, Inc., Burlingame, Calif., USA) following the manufacturer's instructions. Viral antigen foci were counted using AID Reader system (Advance Instrument Device, Strassberg, Germany).

Antibodies

Flavivirus group cross-reactive murine monoclonal antibodies (MAbs, 4G2 recognizing viruses of the four major pathogenic flavivirus serocomplexes) and anti-ZIKV mouse hyper-immune ascetic fluid (MHIAF) were obtained from DVBD, CDC, Fort Collins, Colo. Anti-ZIKV VLP rabbit polyclonal serum was obtained by intramuscular (i.m.) immunization of a non-infectious recombinant adenovirus serotype 5-vectored, MR766 VLP-expressed vaccine candidate (rAdMR1-8; detail in next section). The antibodies were used in the indirect immunofluorescent antibody assay (IFA) and enzyme-linked immunosorbent assays (ELISA) as described below.

Construction of Plasmids

To construct the ZIKV prM and E expressed plasmids, genomic RNA was extracted from 150 µL of Vero cell culture medium infected with MR766, P6-740 and FSS 13025 strains using the QIAmp Viral RNA Kit (Qiagen, Santa Clarita, Calif.). Extracted RNA was eluted in 80 µL of DEPC-treated water (Sigma-Aldrich Inc., St. Louis, Mo.) and used as template in reverse transcription-PCR (RT-PCR) for the amplification of prM and E genes. AfeI, TGA (stop codon) and NotI restriction enzyme sites were incorporated at the 5'- and 3'-termini of the cDNA amplicons, respectively. cDNA amplicons were digested with AfeI and NotI enzymes and inserted into the AfeI and NotI cutting sites of pED1i vector plasmid to obtain the plasmids pEZMR-prME1-8 and pEZP6 3-2. pED1i expressed prME of dengue virus serotype 1 was used as the vector because of the available CMV promoter, Kozak consensus sequence (GCCGCCGCCATGG; SEQ ID NO: 8), a modified Japanese encephalitis signal sequence (JESS), restriction enzyme sites (AfeI and NotI) and BGH poly-A to replace ZIKV prME (FIG. 1A).

Amino acid sequence of prM and E protein of BPH2015 (Brazil/human/2015/BPH2015) was retrieved from GenBank (accession number: KU321639.1) and used as a template to design human codon optimized coding sequence (BZHuprME) that was synthesized commercially (Thermofisher) and inserted between AfeI and NotI sites of pED1i to generate pEBZHu8. A pr1-Ala deletion clone (deletion of the alanine residue at position 1 of prM), pEBZHu2-3, derived from BZHu8 was constructed by a site directed mutagenesis kit (Q5® Site-Directed Mutagenesis Kit, New England BioLabs, Ipswich, Mass.). pAdPL/DEST (Invitrogen, Carlsbad, Calif.) gateway plasmid was used to receive the optimum transcription unit containing ZIKV prME transcriptional unit to generate pAdMR1-8, pAdBZHu8 and pAdBZHu2-3. PRVABC59 (accession number: KU501215.1) virus was used as the challenge virus in the mouse studies. Only one amino acid substitution (E23 of Ile-Val) at the prME region was identified between BPH2015 and PRVABC59 (accession number: KU501215.1) viruses.

Automated DNA sequencing was performed on an ABI Prism 3730 sequencer (Applied Biosystems, Foster City, Calif., USA) and recombinant plasmids with correct prM and E sequences were identified using Lasergene® software (DNASTAR, Madison, Wis.). Plasmids were purified from DH5a E. coli cells using QIAGEN Plasmid Maxi Kit™ (Qiagene, Valencia, Calif.) and reconstituted in DEPC-treated water.

Generation of Non-Infectious Recombinant Expressing prME Containing ZIKV VLPs 293A cells at 85% confluency were transduced with pAdMR1-8 and pAdBZHu2-3 using calcium phosphate precipitation protocol (Invitrogen) to generate rAd5ZMR1-8 (referred to herein as "rAdMR1-8") and rAd5BZHu2-3 (referred to herein as "rAdBZHu2-3") recombinants. rAdMR1-8 and rAdBZHu2-3 were titrated using antigen focus forming test in Vero cells similar to the protocol used to determine the infectivity of ZIKV.

Antigen Production, Secretion Level Characterization and Immunofluorescence Assay (IFA)

To produce VLP antigens, COS-1 cells at a density of $1.5 \times 10^7$ cells/mL were electroporated with 30 µg of ZIKV plasmids following the described protocol (Chang et al., J Virol 74, 4244-4252, 2000). After electroporation, cells from two separate electroporations were combined and seeded into a 150-cm² culture flasks containing 50 mL growth medium. Portions of an electroporated cell suspension were seeded into a Costa 96-well black clear plate (Corning, Corning, N.Y.), 100 µL/well. At 24 to 48 hours after electroporation, cells in the 96-well plate were fixed with 3:1 acetone in PBS at room temperature for 10 minutes, air dried, stored in a Ziploc bag and kept at 4° C. until processing. The remaining cells were allowed to recover overnight at 37° C. The growth medium was replaced the next day with a maintenance medium containing 2-3% FBS and cells were continuously incubated at 28° C. with 5% $CO_2$ for VLP secretion. Tissue-culture media were harvested twice in 5-day intervals after transfection and clarified by centrifugation at 10,000 rpm for 30 minutes at 4° C. and concentrated 40-fold using T19 rotor (Beckman Coulter, Indianapolis Ind.) and re-suspended in TNE buffer (50 mM Tris-HCl (pH 7.4), 100 mM NaCl, 0.1 mM EDTA).

Antigen-capture ELISA as previously described (Chang et al., J Virol 74, 4244-4252, 2000) was performed to detect and quantify the secretion level of VLP antigens harvested from COS-1 cells transfected with ZIKV plasmids. Briefly, flat-bottom 96-well Immulon 2HB™ plates (Thermo Scientifics, Rochester, N.Y.) were coated with 50 µL of polyclonal rabbit anti-ZIKV VLP hyper-immune serum at 1:8,000 in carbonate buffer (15 mM $Na_2CO_3$, 35 mM $NaHCO_3$, pH 9.6), incubated overnight at 4° C., and wells were blocked with 300 µL of blocking buffer (5% skim milk, 0.5% Tween-20 in PBS) for 1 hour at 37° C. Harvested culture media and normal COS-1 culture fluid were titrated two-fold in PBS with 0.05% Tween-20 (wash buffer) and 50 µL were added to wells in duplicate or triplicate, incubated for 2 hours at 37° C., and washed 5 times with 300 µL of wash buffer (BioTek ELx405, Winooski, Vt.). Captured antigens were detected by adding 50 µL of anti-ZIKV MHIAF (1:2000) or a human serum recovered from primary ZIKV infection (1:1000; ZIKV $Nt_{90}$=946.5; dengue serotype 2 $Nt_{90}$<20) in wash buffer, incubated for 1 hour at 37° C., and washed 5 times. Fifty microliters of HRP-conjugated goat anti-mouse IgG or goat anti-human IgG (Jackson ImmunoResearch, Westgrove, Pa., USA) at 1:8,000 in blocking buffer were added to wells and incubated for 1 hour at 37° C. to detect antigen-bound mouse or human IgG, respectively. Subsequently, plates were washed 10 times. Bound conjugate was detected with 100 µL of 3,3',5,5'-tetramethylbenzidine substrate (Enhanced K-Blue® TMB, NEOGEN® Corp., Lexington, Ky., USA), incubated at room temperature for 10 minutes, and stopped with 50 µL of 2N $H_2SO_4$. Reactions were measured at $A_{450}$ using BioTek Synergy HTX™ microplate reader (BioTek). Endpoint antigen secretion titers from two or three independent experiments were determined, as deduced from twice the average optical density (OD) of negative control antigen (P/N=2), after curve-fitting using a sigmoidal dose-response equation in GraphPad Prism version 6.0 (GraphPad Software, Inc., La Jolla, Calif., USA).

For IFA, ZIKV MHIAF and 4G2 were diluted 1:200 in PBS and 50 µL/well of each were used to stain acetone fixed cells in a 96-well plate at 37° C. for 1 hour in a humidified Ziploc bag, then washed five time with 300 µL of PBS. Fifty µL of a goat anti-mouse-FITC conjugated IgG (Jackson ImmunoResearch, Westgrove, Pa., USA) at 1:6,000 in blocking buffer were added to wells and incubated at 37° C. for one hour in a humidified Ziploc bag to detect cell-bound mouse IgG, washed four times with 300 µL of PBS, incubated with 300 µL of 0.0005% Evan's blue in PBS at room temperature for 5 minutes and washed two additional times in PBS. Fifty µL of mounting medium (4% of DABCO; 1,4-Diazabicyclo-(2,2,2) Octoane dissolved in 80% glycerol-20% PBS) were added to wells and cells visualized using 20× objective and recorded using a fluorescent microscope (AXiovert 200M, Zeiss, Thornwood, N.Y.).

Mouse Experiment

To establish immunogenicity and vaccine efficacy models, the ICR (outbreed mice, Harlan Sprague Dawley, Madison, Wis.) and AG129 mice ($\alpha$, $\beta$ and $\gamma$ interferon receptor-deficient mice, in-house colony) were used at between 4 to 8 weeks old. Five groups of five female ICR mice per group or AG129 mice (3 male and 2 females or 2 males and 3 females) at age between 4 to 8 weeks old were injected intraperitoneally (i.p.) with $10^7$, $10^6$, $10^5$, $10^4$ or $10^3$ pfu/100 µL (diluted in PBS) of MR766 viruses, respectively. Seven groups of five female ICR mice or AG129 mice at age between 4 to 8-week old (3 male and 2 females or 2 males and 3 females) were injected i.p with $10^7$, $10^6$, $10^5$, $10^4$ $10^3$, $10^2$ or $10^0$ pfu/100 µL (diluted in PBS) of PRVABC59 viruses, respectively. Experimental mice were observed daily and percent survival in each group was recorded for 21 days. All virus challenged ICR mice, regardless of viral strain and dosage used, survived challenge with no observable morbidity for 21 days. All virus challenged AG129 mice, regardless its sex, viral strain and dosage used, showed 100 percent mortality between day-6 and day-21. Thus, we chose ICR and AG129 mice to evaluate immunogenicity and vaccine efficacy, respectively.

Groups of 4 to 8-week-old female ICR mice, 5 mice per group, were injected intramuscularly with rAdMR1-8 at week-0 at a dose of $10^5$ or $10^6$ transduction units (TU)/100 µL (diluted in PBS) divided between the right and left quadriceps muscle. Similarly, groups of 4 to 8-week-old (2 males and 3 females or 3 males and 2 females) AG129 mice were i.m. injected at week-0 at a dose of $10^5$ or $10^6$ transduction units (TU)/100 µL in PBS. ICR Mice were bled from the tail vein at day 7 and every 4 weeks post vaccination. Serum specimens from individual mice were stored separately at 4° C. to determine the total IgG and neutralization antibody by IgG antibody-captured ELISA (GAC-ELISA) and antigen focus-reduction micro-neutralization test (FRpNT), respectively. Two groups of vaccinated and one group of age-matched naïve AG129 mice were challenged by i.p. with 1,000 ffu of PRVABC56 in 100 µL of PBS at 4 weeks post-vaccination (PV) to determine the protective efficacy of the vaccine. Prior to virus challenge, at day 7, 4 weeks PV and 4 weeks post viral challenge (PC) of survival mice, serum specimens were collected from tail vein and stored at 4° C. to determine the total IgG and neutralization antibody. Percent survival in mice was observed two to four times daily up to 21 days. ZIKV-specific total IgG antibodies by ELISA and FRpNT were measured as described in the following section.

ELISA

Mouse serum specimens were assayed for the presence of ZIKV-specific total IgG with the same Ag-capture ELISA protocol described above with minor modifications. MR766 and BHP2015-VLP antigens were standardized by Ag-capture ELISA at a single concentration producing an OD of 1.0, within the region of antigen excess near the upper asymptote of the sigmoidal antigen dilution curve, and were used to determine total IgG titer after appropriate dilutions. Individual serum specimens, initially diluted at 1:1,000, were titrated two-fold and added to wells in duplicate and incubated for 1 hour at 37° C. Pre-vaccination mouse sera were included as negative controls. Incubations with conjugate and substrate were carried out according to the standard Ag-capture ELISA as above. $OD_{450}$ values were modeled as non-linear functions of the log 10 serum dilutions using a sigmoidal dose-response (variable slope) equation and endpoint antibody titers were determined at the dilutions where the OD value was twice the average OD of negative control. Each serum specimen was tested in two or three independent experiments.

Virus Neutralization

To measure the neutralizing ability of the immune mice serum specimen against MR766 and PRVABC56 representing prototype African genotype and a current circulating Asian genotype strains, an antigen focus-reduction micro-neutralization test (FRµNT) was utilized as previously described (Crill et al., *Front Immunol* 3, 334, 2012; Galula et al., *J Virol* 88, 10813-10830, 2014). Briefly, $2.475 \times 10^4$ Vero cells/well were seeded into flat-bottom 96-well Costar® cell culture plates (Corning Inc., Corning, N.Y., USA) and incubated for 16 hours overnight at 37° C. with 5% $CO_2$. Serum specimen were initially diluted at 1:10, heat-inactivated for 30 minutes at 56° C., titrated two-fold to a 40 µL volume, and 320 pfu/40 µL of MR766 or PRV-ABC56 (8% normal human serum in DMEM) was added to each dilution. The mixtures were then incubated for 1 hour at 37° C. After incubation, 25 µL of the immune complexes were inoculated in duplicate into plates containing a Vero cell monolayer. Plates were incubated for 1 hour at 37° C. with 5% $CO_2$ and rocked every 10 minutes to allow infection. Overlay medium containing 1% methylcellulose (Sigma-Aldrich Inc., St. Louis, Mo., USA) in DMEM with 2% FBS was added and plates were incubated at 37° C. with 5% $CO_2$. Forty hours later, plates were washed, fixed with 75% acetone in PBS and air-dried. Immunostaining was performed by adding anti-ZIKV MHIAF at 1:1,000 in PBS and incubated for 60 minutes at 37° C., washing and adding goat anti-mouse IgG-HRP at 1:200 in 5% skim milk in PBS and incubated for 30 minutes at 37° C. Infection foci were visualized using peroxidase substrate kit Vector® VIP SK-4600 (Vector Laboratories, Inc., Burlingame, Calif.) following the manufacturer's instructions. FRµNT titers were calculated for each virus relative to a virus only control back-titration. Titers of exact 90%, 75% or 50% reduction of infection foci ($FR\mu NT_{90}$, $FR\mu NT_{75}$ and $FR\mu NT_{50}$ titer) were modeled using a sigmoidal dose-response (variable slope) formula. All values were taken from the average of two independent experiments. Viral antigen foci were counted using AID Reader system (Advance Instrument Device, Strassberg, Germany).

Example 2: A Recombinant ZIKV Vaccine that Prevents ZIKV Infection and Mortality in an Animal Model This example describes an adenovirus-vectored ZIKV vaccine that is capable of eliciting protective immunity and prevents ZIKV infection as early as seven days post-immunization.

Figure 1B:
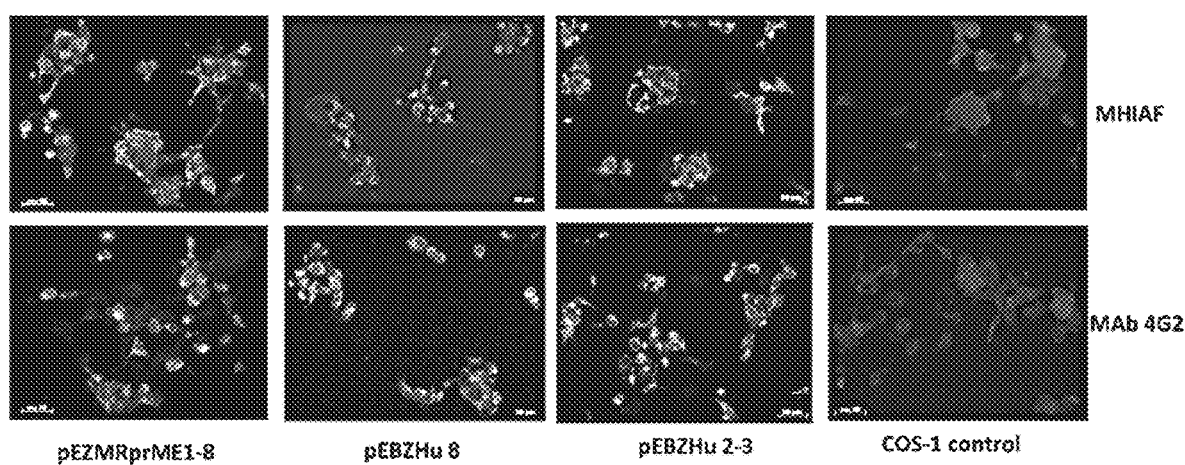
Figure 1C:
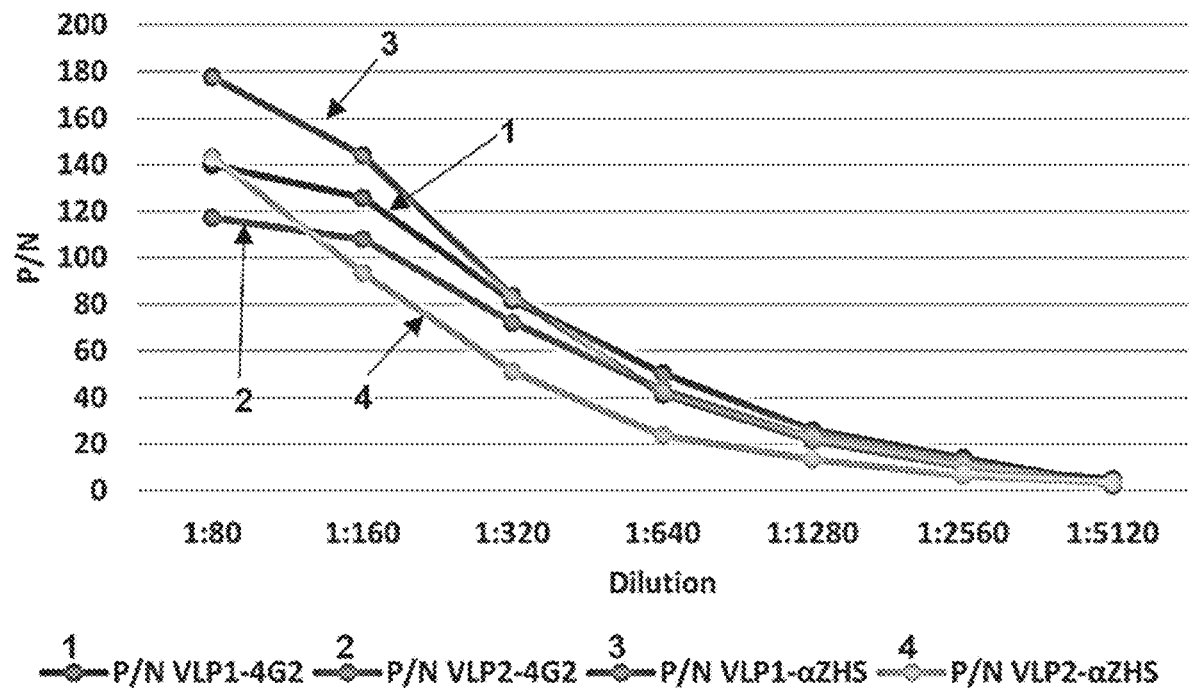
Figure 1D:
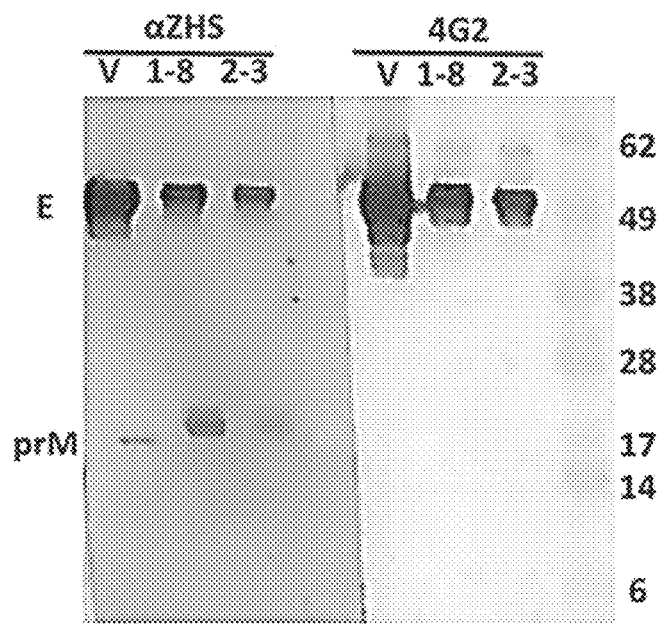
Figure 2A:
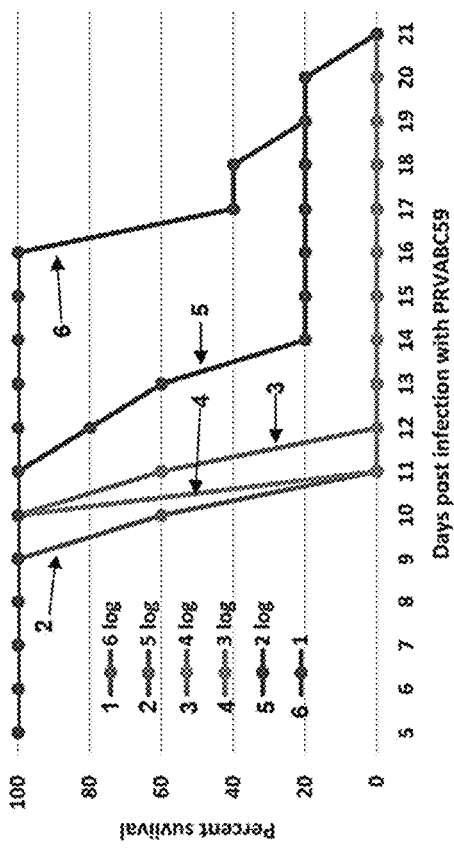
FIGS. 2A-2D: Characterization of AG129 mouse as the disease and vaccine efficacy model. Cumulative survival rate of AG129 mice challenged with various doses of MR766 (FIG. 2A) and PRVABC59 (FIG. 2B) virus. In vivo protective efficacy of a ZIKV vaccine is dose-dependent (FIG. 2C). The protective efficacy of a non-infectious recombinant adenovirus-vector ZIKV vaccine candidate (rAdMR1-8) was determined by challenging four weeks post-vaccinated immunized AG129 mice with $10^3$ focus forming units (ffu) of PRVABC59 virus. Mice that had received $10^6$, but not $10^5$ transduction units (TU) of candidate vaccine were fully protective from viral challenge. ZIKV-specific reactivity of pre-challenge and post challenge serum specimens immunized with $10^6$ TU of vaccine was characterized by Western blot analysis (FIG. 2D). E and prM bands were detected by pre- and post-challenge pooled serum in purified virions, 1-8 and 2-3 VLPs. Mature M protein was only detected by post-challenge serum in purified virions. 4WPC=4 weeks post-challenge; 4WPV=4 weeks post-vaccination.
Figure 2C:
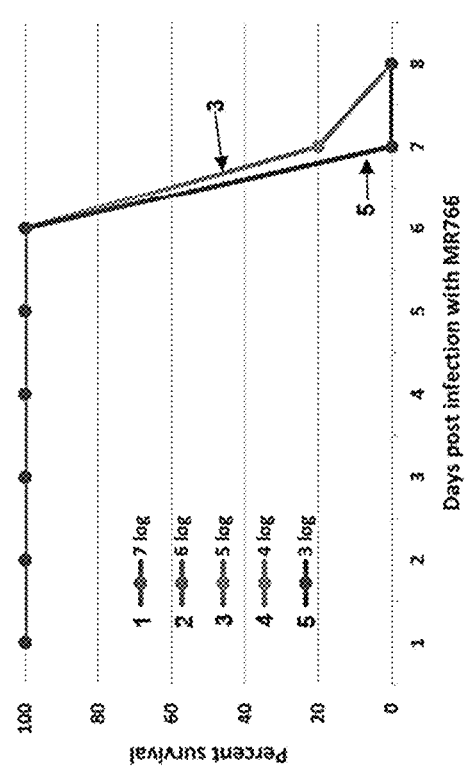
Figure 2B:
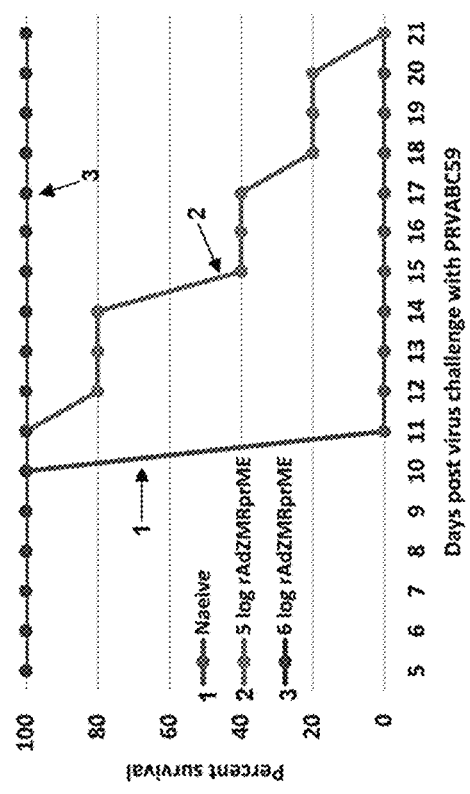
Figure 2D:
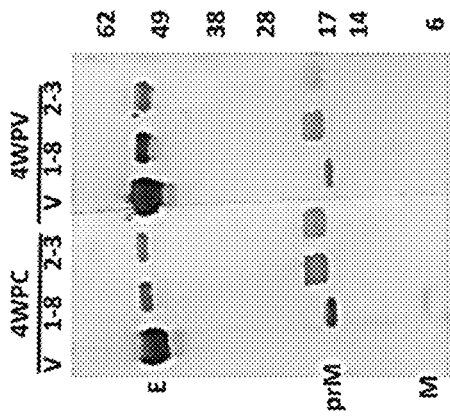
Figures 4C, 4D:
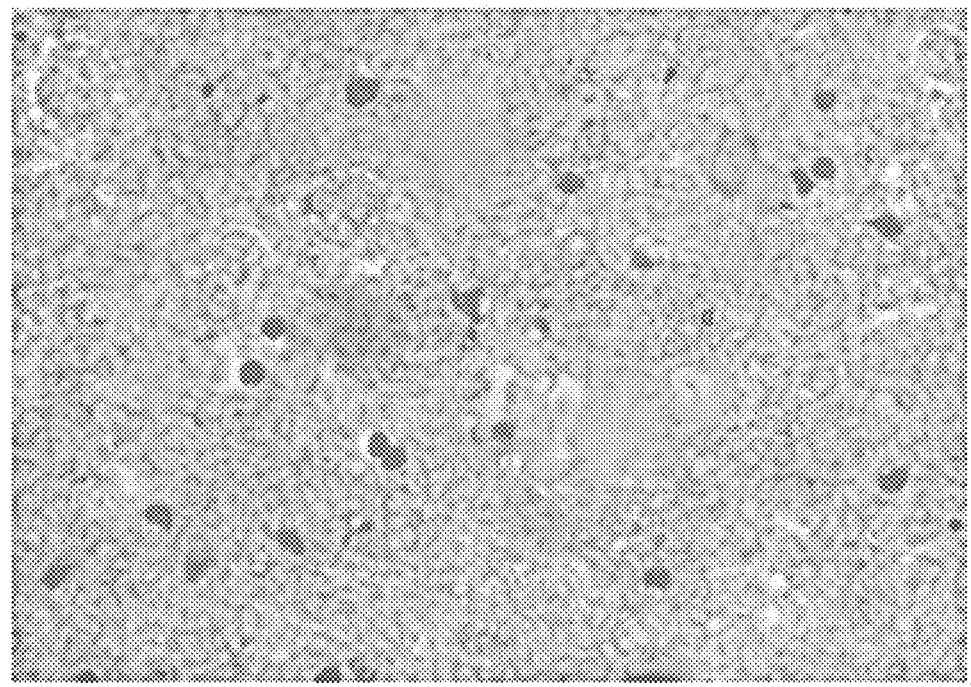
Figures 5A, 5B:
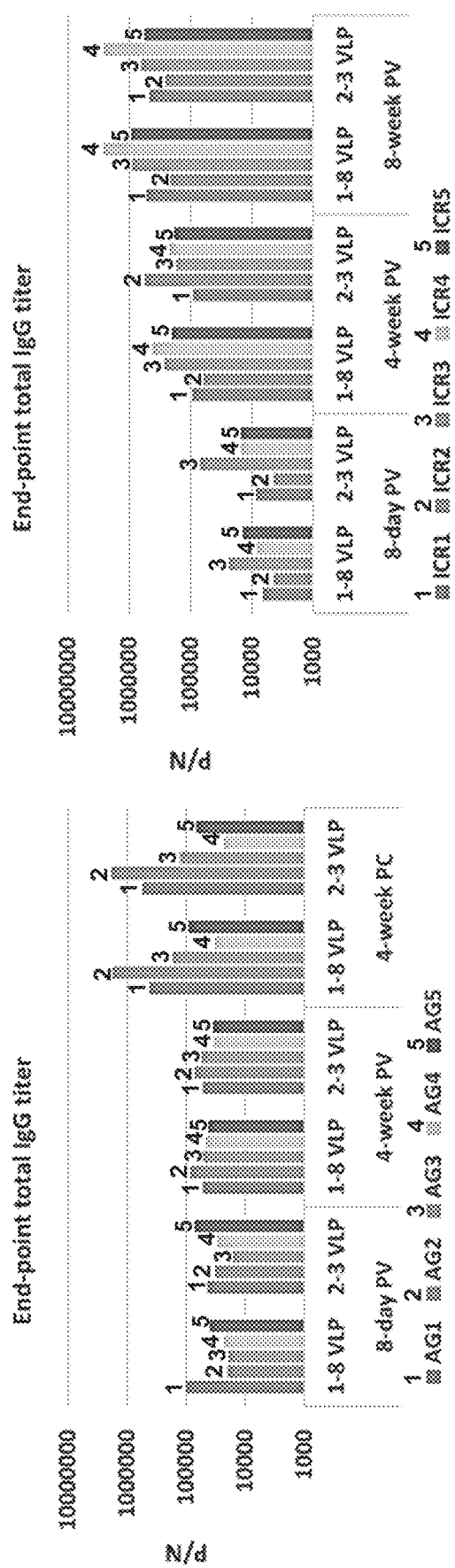
FIGS. 5A-5B: Total IgG titers in AG129 (FIG. 5A) and ICR (FIG. 5B) mice immunized with $10^6$ transduction units of rAdMR1-8 vaccine. Only AG129 mice were challenged with PRC59 virus at four weeks post-vaccination. IgG reactivity was determined using MR766 (1-8 VLP) and BPH2015 (2-3 VLP) antigens. For FIG. 5A, bars are from left to right: AG1, AG2, AG3, AG4 and AG5. For FIG. 5B, bars are from left to right: ICR1, ICR2, ICR3, ICR4 and ICR5.

VLPs of several non-ZIKV flaviviruses have been previously generated (Chang et al., *J Virol* 74, 4244-4252, 2000; Davis et al., *J Virol* 75, 4040-4047, 2001; Hunt et al., *J Virol Methods* 97, 133-149, 2001). The present study includes the construction of three prME expression plasmids derived from three ZIKV strains (MR766, P6-740 and BPH2015). MR766 (the prototype African genotype virus; AY632535) and P6-740 (the prototype Asian genotype virus; HQ234499) prME coding sequences were directly amplified from viral RNA. Human codon optimized prME sequences were designed and synthesized commercially to express the BPH2015 (current circulating Asian genotype virus; KU321639) prME coding region. Sequence verified plasmid clones pEZMRprME1-8 (FIG. 1A), pEZP6 3-2 and pEBZHu8 containing MR766, P6-740 and human codon optimized BPH2015 prME gene insert, respectively, were electroporated into COS-1 cells. Plasmid-transformed COS-1 cells and culture media were harvested at 24 hours and twice every 5 days after electroporation, respectively, to determine antigen expression by indirect fluorescent antibody assay (IFA), and the level of VLP secretion by antigen-capture ELISA (AG-ELISA) and Western blot (FIGS. 1B-1D). All transcription units have the identical regulatory elements for transcriptional (CMV promoter and BGH(A)n), translational (Kozak consensus sequence; GCCGCCGCCATGG, SEQ ID NO: 8) and protein processing (modified Japanese encephalitis virus signal sequence) with a similar signalase cleavage site potential predicted by the Signal IP 4.1 program (Table 1). The end-point titer of VLPs secreted from COS-1 cells were 274.8, 4.0 and 58.80 from pEZMRprME1-8, pEZP6 3-2 and pEBZHu8, respectively. The pEZP6 3-2 clone secreted the fewest VLPs. The pEBZHu8 clone secreted 4-fold less VLPs than the pEZMRprME1-8 clone. A pr1-A deletion clone derived from pEBZHu8, pEBZHu2-3, exhibited 3-fold increased VLP secretion to the end-point titer of 194.6 (Table 1), compared to the pEBZHu8 clone transformed COs-1 cells. Thus, the studies disclosed herein focused on the pEZMRprME1-8 and pEBZHu2-3 constructs. pEZMRprME1-8, pEBZHu8 and pEBZHu2-3 transformed COS1 cells were IFA positive (FIG. 1B) using Zika virus recovered convalescent human serum (αZHS, neutralization (Nt) antibody titer-45,960 against MR766 and Nt=19.4 against dengue virus serotype 2 16681) and MAb 4G2. Using a rabbit polyclone anti-ZIKV antibody as the capture antibody to capture VLPs (1:40 concentrated culture media harvested every 5 days from two independent pEZMRprME1-8 plasmids transformed cells) and 4G2 or αZHS as a detector in the Ag-ELISA, 4G2 and αZHS detected both concentrated VLPs equally well (FIG. 1C). By Western blot, 4G2 detected only E protein (predicted MW of 54.6 kd) from purified MR 766 virus, pEZMRprME1-8 and pEBZHu2-3 VLPs. In addition to E, αZHS detected the un-processed prM protein (predicted MW of 19.0 kd).

TABLE 1

| | | Signal sequence cleavage potential predicted by Signal IP 4.1 program | | | |
|---|---|---|---|---|---|
| Gene | Character | Signal IP 4.1 prediction Predicted furin and signalase cleavage site↓ | SEQ ID NO: | Cleavage potential ID | Plasmid clone (AG-ELISA) |
| MR766 furin | Furin cleavage motif + ZIKV SS | RKEKKRR↓<u>GADTSIGIVGLLLTTAMA</u>↓AEITRRGSAYYMYLDRSD | 9 | 0.49 | (N.D.) |
| MR766 after furin | ZIKV SS | <u>GADTSIGIVGLLLTTAMA</u>↓AEITRRGSAYYMYLDRSD | 10 | 0.481 | (N.D.) |
| P6-740 after furin | ZIKV SS | <u>GADTSIGIVGLLLTTAMA</u>↓AEVTRRGSAYYMYLDRND | 11 | 0.485 | pEZP6-740 (4.00) |
| BPH2015 furin | Furin cleavage motif + ZIKV SS | RKEKKRR↓<u>GADTSVGIVGLLLTTAMA</u>↓AEVTRRGSAYYMYLDRND | 12 | 0.518 | (N.D.) |
| BPH2015 after furin | ZIKV SS | <u>GADTSVGIVGLLLTTAMA</u>↓AEVTRRGSAYYMYLDRND | 13 | 0.493 | (N.D.) |
| JESSMR766 | Modified JE SS | <u>MGKRSAGSIMWLASLAVVIAGTSA</u>↓AEITRRGSAYYMYLDRSD | 14 | 0.797 | pEZMRprME1-8 (274.90) |
| JESSBPH2015 | Modified JE SS | <u>MGKRSAGSIMWLASLAVVIAGTSA</u>↓AEVTRRGSAYYMYLDRND | 15 | 0.805 | (N.D.) |
| JESSd1ABPH2015 | Delete A at pr1 | <u>MGKRSAGSIMWLASLAVVIAGTSA</u>↓EVTRRGSAYYMYLDRND | 16 | 0.747 | (N.D.) |
| JESSd3VBPH2015 | Delete V at pr3 | <u>MGKRSAGSIMWLASLAVVIAGTSA</u>↓AETRRGSAYYMYLDRND | 17 | 0.756 | (N.D.) |
| JESS + V | V insertion | <u>MGKRSAGSIMWLASLAVVIAGTSA</u>↓AVEVTRRGSAYYMYLDRND | 18 | 0.774 | pEBZHu8 (58.80) |

TABLE 1 -continued

Signal sequence cleavage potential predicted by Signal IP 4.1 program

| Gene | Character | Signal IP 4.1 prediction<br>Predicted furin and signalase cleavage site↓ | SEQ<br>ID<br>NO: | Cleavage<br>poten-<br>tial<br>ID | Plasmid<br>clone<br>(AG-ELISA) |
|---|---|---|---|---|---|
| JESS-A + V | A dele-<br>tion<br>and<br>V insertion | MGKRSAGSIMWLAS

TABLE 2

Neutralizing antibodies of post-vaccination (PV) and post-viral (PC) challenged
AG129 mouse serum specimens collected post viral challenge

| | | 8-day PV-FRµNT | | | | | |
| | | ZIKV MR766 | | | ZIKV PR59 | | |
| Mouse | Dose | 90 | 75 | 50 | 90 | 75 | 50 |
|---|---|---|---|---|---|---|---|
| AG1 | 1E+6TU | 139 | 271 | 524 | <20 | 24 | 46 |
| AG2 | | 24 | 55 | 222 | <20 | 23 | 58 |
| AG3 | | 72 | 159 | 269 | <20 | 10 | 55 |
| AG4 | | 80 | 187 | 439 | <20 | 10 | 54 |
| AG5 | | 69 | 180 | 471 | <20 | 27 | 62 |
| | Average | 77 | 170 | 385 | | 15 | 55 |
| AG1 | 1E+E5 | <20 | <20 | <20 | <20 | <20 | <20 |
| AG2 | | <20 | <20 | <20 | <20 | <20 | <20 |
| AG3 | | <20 | <20 | <20 | <20 | <20 | <20 |
| AG4 | | <20 | <20 | <20 | <20 | <20 | <20 |
| AG5 | | <20 | <20 | <20 | <20 | <20 | <20 |

| | | 4-week PV-FRµNT | | | | | |
| | | ZIKV MR766 | | | ZIKV PR59 | | |
| Mouse | Dose | 90 | 75 | 50 | 90 | 75 | 50 |
|---|---|---|---|---|---|---|---|
| AG1 | 1E+6TU | 59 | 183 | 552 | <20 | 26 | 54 |
| AG2 | | 142 | 258 | 5120 | <20 | 30 | 82 |
| AG3 | | 36 | 130 | 411 | <20 | 28 | 112 |
| AG4 | | 91 | 259 | 778 | <20 | 32 | 122 |
| AG5 | | 79 | 237 | 785 | <20 | 33 | 116 |

| | | 4-week PV-FRµNT | | | | | |
| | | ZIKV MR766 | | | ZIKV PR59 | | |
| Mouse | Dose | 90 | 75 | 50 | 90 | 75 | 50 |
|---|---|---|---|---|---|---|---|
| | Average | 81 | 213 | 1529 | | 30 | 97 |
| AG1 | 1E+E5 | <20 | <20 | <20 | <20 | <20 | <20 |
| AG2 | | <20 | <20 | <20 | <20 | <20 | <20 |
| AG3 | | <20 | <20 | <20 | <20 | <20 | <20 |
| AG4 | | <20 | <20 | <20 | <20 | <20 | <20 |
| AG5 | | <20 | <20 | <20 | <20 | <20 | <20 |

| | | 4-week PC-FRµNT | | | | | |
| | | ZIKV MR766 | | | ZIKV PR59 | | |
| Mouse | Dose | 90 | 75 | 50 | 90 | 75 | 50 |
|---|---|---|---|---|---|---|---|
| AG1 | 1E+6TU | 21 | 83 | 452 | 10 | 24 | 59 |
| AG2 | | 21 | 105 | 575 | 10 | 31 | 81 |
| AG3 | | 170 | 356 | 5120 | 74 | 162 | 442 |
| AG4 | | 10 | 65 | 203 | 10 | 10 | 54 |
| AG5 | | 71 | 170 | 491 | 36 | 66 | 133 |
| | Average | 59 | 156 | 1368 | 55 | 71 | 154 |

| | | 8-day PV-FRµNT | | | | | |
| | | ZIKV MR766 | | | ZIKV PR59 | | |
| Mouse | Dose | 90 | 75 | 50 | 90 | 75 | 50 |
|---|---|---|---|---|---|---|---|
| ICR1 | 1E+6TU | 43 | 79 | 177 | <20 | 28 | 84 |
| ICR2 | | 59 | 97 | 141 | <20 | 10 | 79 |
| ICR3 | | 413 | 654 | 1059 | <20 | 10 | 176 |
| ICR4 | | 228 | 310 | 397 | <20 | 38 | 161 |
| ICR5 | | 101 | 221 | 513 | <20 | 48 | 193 |
| | Average | 169 | 272 | 457 | | 23 | 139 |

| | | 8-day PV-FRµNT | | | | | |
| | | ZIKV MR766 | | | ZIKV PR59 | | |
| Mouse | Dose | 90 | 75 | 50 | 90 | 75 | 50 |
|---|---|---|---|---|---|---|---|
| ICR1 | 1E+E5 | <20 | <20 | <20 | <20 | <20 | <20 |
| ICR2 | | <20 | <20 | <20 | <20 | <20 | <20 |

TABLE 2-continued

Neutralizing antibodies of post-vaccination (PV) and post-viral (PC) challenged
AG129 mouse serum specimens collected post viral challenge

| | | | | | | | |
|---|---|---|---|---|---|---|---|
| ICR3 | | <20 | <20 | <20 | <20 | <20 | <20 |
| ICR4 | | <20 | <20 | <20 | <20 | <20 | <20 |
| ICR5 | | <20 | <20 | <20 | <20 | <20 | <20 |

4-week PV-FRµNT

| | | ZIKV MR766 | | | ZIKV PR59 | | |
|---|---|---|---|---|---|---|---|
| Mouse | Dose | 90 | 75 | 50 | 90 | 75 | 50 |
| ICR1 | 1E+6TU | 733 | 1161 | 5120 | 35 | 69 | 131 |
| ICR2 | | 471 | 1101 | 2378 | 10 | 57 | 126 |
| ICR3 | | 404 | 1395 | 5120 | 42 | 103 | 259 |
| ICR4 | | 246 | 1860 | 5120 | 44 | 126 | 401 |
| ICR5 | | 915 | 5120 | 5120 | 73 | 171 | 436 |
| Average | | 674 | 2127 | 4572 | 41 | 105 | 271 |
| ICR1 | 1E+E5 | <20 | <20 | 23 | <20 | <20 | <20 |
| ICR2 | | <20 | <20 | 32 | <20 | <20 | <20 |
| ICR3 | | <20 | <20 | 37 | <20 | <20 | <20 |
| ICR4 | | <20 | <20 | 22 | <20 | <20 | <20 |
| ICR5 | | <20 | <20 | 28 | <20 | <20 | <20 |

8-week PV-FRµNT

| | | ZIKV MR766 | | | ZIKV PR59 | | |
|---|---|---|---|---|---|---|---|
| Mouse | Dose | 90 | 75 | 50 | 90 | 75 | 50 |
| ICR1 | 1E+6TU | 1184 | 2314 | 5120 | 415 | 699 | 2306 |
| ICR2 | | 1001 | 1916 | 5120 | 235 | 574 | 1986 |
| ICR3 | | 478 | 994 | 5120 | 224 | 417 | 917 |
| ICR4 | | 1262 | 5120 | 5120 | 302 | 634 | 1486 |
| ICR5 | | 1423 | 5120 | 5120 | 551 | 1006 | 2529 |
| Average | | 1070 | 3093 | 5120 | 345 | 666 | 1845 |
| ICR1 | 1E+E5 | <20 | <20 | <20 | <20 | <20 | <20 |
| ICR2 | | <20 | <20 | <20 | <20 | <20 | <20 |
| ICR3 | | <20 | <20 | <20 | <20 | <20 | <20 |
| ICR4 | | <20 | <20 | <20 | <20 | <20 | <20 |
| ICR5 | | <20 | <20 | <20 | <20 | <20 | <20 |

12-week PV-FRµNT

| | | ZIKV MR766 | | | ZIKV PR59 | | |
|---|---|---|---|---|---|---|---|
| Mouse | Dose | 90 | 75 | 50 | 90 | 75 | 50 |
| ICR1 | 1E+6TU | 1462 | 2730 | 4973 | 536 | 1100 | 2278 |
| ICR2 | | 1288 | 1866 | >5120 | 448 | 813 | 1447 |
| ICR3 | | 2221 | 2372 | 2602 | 341 | 837 | 1908 |
| ICR4 | | 2458 | 2754 | >5120 | 408 | 1066 | 2435 |
| ICR5 | | 1753 | 3249 | >5120 | 679 | 1628 | 3508 |
| Average | | 1836 | 2594 | 4587 | 482 | 1089 | 2315 |

Since both male and female mice are similarly susceptible to MR766 and PR59 infection and MR766 is more virulent than PR59 virus, it was investigated whether the protective efficacy would be different among them. Two groups of AG129 mice (6 males plus 6 females per group) were immunized with a single $10^6$ TU of rAdMR1-8 vaccine candidate. Two age- and sex-matched naïve control and two vaccinated groups were challenged on the same day with 200 and 840 ffu/100 µL of MR766 and PR59 virus, determined precisely by titrating the duplicate of both challenge viruses, respectively. Serum specimens were collected from naïve and vaccinated mice on day 2, 3, 5, 6, 7 and 9 PC for the viremic study. Vaccinated mice were virus isolation negative throughout 9 collection days for both challenge groups (Table 3). MR766 challenged morbid-bound naïve mice were euthanized on day 6 PC. The viremic titers in this mouse group ranged from $3.17 \times 10^7$ to $8.53 \times 10^6$ ffu/mL throughout collection period. PR59 challenged naïve mice had no signs of illness for the first 9-day PC and virus was detected between day-2 and day-6 but not on day-7 and day-9 collection. The average viremic titers ranged from $1.62 \times 10^5$ to $4.8 \times 10^4$, significantly lower titer than MR766 challenged mice (Table 3).

TABLE 3

Post-challenge viremic viral titers determined from subset of mice

| | Day post challenge viremic titer (ffu/mL) | | | | | |
|---|---|---|---|---|---|---|
| Treatment | 2 | 3 | 5 | 6 | 7 | 9 |
| Naïve/ MR766 | $6.40 \times 10^3$ | $3.07 \times 10^7$ | $3.07 \times 10^7$ | $1.74 \times 10^7$ | N/A | N/A |
| | $6.40 \times 10^5$ | $3.07 \times 10^7$ | $1.13 \times 10^7$ | $8.19 \times 10^6$ | N/A | N/A |
| | $3.20 \times 10^3$ | $3.07 \times 10^7$ | $3.17 \times 10^7$ | N/A | N/A | N/A |
| Average | $1.62 \times 10^5$ | $2.30 \times 10^7$ | $1.84 \times 10^7$ | $8.53 \times 10^6$ | | |
| Naïve/ PR59 | $1.28 \times 10^5$ | 0.00 | $3.84 \times 10^4$ | $8.32 \times 10^4$ | — | — |
| | $1.41 \times 10^5$ | $4.80 \times 10^3$ | $8.32 \times 10^4$ | $4.48 \times 10^4$ | — | — |
| | $2.18 \times 10^5$ | $1.02 \times 10^6$ | $2.24 \times 10^4$ | $1.06 \times 10^5$ | — | — |

TABLE 3-continued

Post-challenge viremic viral titers determined from subset of mice

| | Day post challenge viremic titer (ffu/mL) | | | | | |
|---|---|---|---|---|---|---|
| Treatment | 2 | 3 | 5 | 6 | 7 | 9 |
| Average | $1.62 \times 10^5$ | $3.43 \times 10^5$ | $4.80 \times 10^4$ | $7.79 \times 10^4$ | — | — |
| rAdMR1-8/ | | | | | | |
| MR766 | — | — | — | — | — | — |
| rAdMR18/ | | | | | | |
| PR59 | — | — | — | — | — | — |

Naïve/MR766 challenged mice were euthanized on day-6 post-challenge.
N/A = not available
— = virus undetected Example 3: Generation and Characterization of ZIKV VLPs with Mutations at Positions 106 and 107 of the E Protein Previous studies of dengue virus identified immunodominant cross-reactive epitopes within the E glycoprotein that are associated with immune enhancement. Mutation of particular residues of the E protein, including positions 106 and 107, led to a reduction in cross-reactivity amongst dengue virus serotypes (WO 2013/059493), which is an important safety feature for a flavivirus vaccine. The studies described in this example introduce this safety feature into the ZIKV VLP constructs.

Using pEBZHu2-3 as a template and the mutagenesis primers listed in Table 4, five different mutant constructs were generated that contain mutations in the codons for E protein residues 106 and 107, resulting in substitution of the native glycine and leucine (GL) residues at E106/107 with lysine and aspartic acid (KD); arginine and aspartic acid (RD); arginine and histidine (RH); glutamic acid and aspartic acid (ED); or glutamic acid and arginine (ER). VLP secretion of each mutant was tested as described in Example 1. The results demonstrated that the KD mutant exhibited the highest levels of VLP secretion (Table 4). Therefore, the same mutations were introduced into the pEZMRprME 1-8 construct.

TABLE 4

Primer sequences to derive E 106/107 mutants and ranking of mutated VLPs secretion

| pEBZHu2-3 as the template | SEQ ID NO | Ranking |
|---|---|---|
| GL106/107KD CAATGGCTGCaaggacTTTGGCAAGGGCAGCC | 24 | 1 |
| GL106/107RD CAATGGCTGCcgagacTTTGGCAAGGGCAGCCTCG | 25 | 2 |
| GL106/107RH CAATGGCTGCcgacatTTTGGCAAGGGCAGCC | 26 | 3 |
| GL106/107ED CAATGGCTGCgaagatTTTGGCAAGGGCAG | 27 | 4 |
| GL106/107ER CAATGGCTGCgaacgaTTTGGCAAGGGCAGC | 28 | 5 |
| pEZMRprME 1-8 as the template | | |
| GL106/107KD GAAACGGTTGTaaggaTTTTGGCAAAGGGAG | 29 | n.a. |

The wild-type and mutant ZIKV VLPs were tested for cross-reactivity with a panel of flavivirus E protein-specific murine monoclonal antibodies. COS-1 cells ($2 \times 10^7$/ml) were electroporated with 30 μg of pEZMR766 prME 1-8 (wt), pEZMR KD, pEBzHu 2-3 (wt) and pEBzHu KD. Tissue culture supernatants were harvested and clarified at 10,000 rpm for 30 minutes. The clarified supernatants were used to compare cross-reactivities of the ZIKV VLPs against a panel of E-specific murine monoclonal antibodies (MAbs). As shown in Table 5, the E106/107 KD mutants drastically reduced 5 group cross-reactive MAbs, but did not alter ZIKV virus-specific MAbs.

TABLE 5

E106/107 mutations of ZIKV VLPs influence monoclonal antibodies

| Antibodies | MHIAF | 2H2 | 4G2 | 6B6C-1 | 4A1B-9 | 23-1 |
|---|---|---|---|---|---|---|
| Source of immunogen | Zika MR766 | DENV-2 | DENV-2 | SLEV | MVEV | WNV |
| Antigenic group | | DENV SC | Group | Group | Group | Group |
| Antigen specificity | | prM | E | E | E | E |
| Antibody end-point titers | | | | | | |
| MR766wt VLPs | >2,187,000 | <1,000 | >2,187,000 | >2,187,000 | 81,000 | >2,187,000 |
| MR766KD VLPs | 243,000 | <1,000 | <1,000 | 27,000 | <1,000 | <1,000 |

TABLE 5-continued

E106/107 mutations of ZIKV VLPs influence monoclonal antibodies

| | | | | | | |
|---|---|---|---|---|---|---|
| Fold changes | >9 | NA | >2,187 | >81 | >81 | >2,187 |
| BzHuwt VLPs | 243,000 | <1,000 | 729,000 | 729,000 | 81,000 | >2,187,000 |
| BzHuKD VLPs | 243,000 | <1,000 | <1,000 | 9,000 | <1,000 | <1,000 |
| Fold changes | 0 | NA | >729 | 81 | >81 | >2,187 |

| Antibodies | 23-2 | 1B7 | D35C9-1 | 6B4A-10 | 9D12 | 1A1D-2 |
|---|---|---|---|---|---|---|
| Source of immunogen | JEV | DENV-3 | DENV-4 | JEV | DENV-1 | DENV-2 |
| Antigenic group | Group | DENV SC | DENV SC | JEV SC | DENV-1, -2, -4 | DENV-1, -2, -3 |
| Antigen specificity | E | E | E | E | E | E |
| MR766wt VLPs | >2,187,000 | <1,000 | <1,000 | 9,000 | <1,000 | <1,000 |
| MR766KD VLPs | 3,000 | <1,000 | <1,000 | 27,000 | <1,000 | <1,000 |
| Fold changes | >729 | NA | NA | 3 | NA | NA |
| BzHuwt VLPs | 729,000 | <1,000 | <1,000 | 3,000 | <1,000 | <1,000 |
| BzHuKD VLPs | 9,000 | <1,000 | <1,000 | 9,000 | <1,000 | <1,000 |
| Fold changes | 81 | NA | NA | 3 | NA | NA |

| Antibodies | 14H5 | T5-1 | 3H5 | D6-8A1 | INB9164 | INB9165 |
|---|---|---|---|---|---|---|
| Source of Antibodies immunogen | JEV 14H5 | JEV T5-1 | DENV-2 3H5 | DENV-3 D6-8A1 | ZIKV INB9164 | ZIKV INB9165 |
| Antigenic group | JEV, DENV | JEV, DENV-2 | DENV-2 | DENV-3 | ZIKV | ZIKV |
| Antigen specificity | E | E | E | E | E | E |
| MR766wt VLPs | <1,000 | 9,000 | <1,000 | <1,000 | 2,187,000 | 2,187,000 |
| MR766KD VLPs | <1,000 | 9,000 | <1,000 | <1,000 | 729,000 | 729,000 |
| Fold changes | NA | 0 | NA | NA | 3 | 3 |
| BzHuwt VLPs | <1,000 | 9,000 | <1,000 | <1,000 | 729,000 | 729,000 |
| BzHuKD VLPs | <1,000 | 3,000 | <1,000 | <1,000 | 729,000 | 729,000 |
| Fold changes | NA | 3 | NA | NA | 0 | 0 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A vector comprising a nucleic acid molecule comprising a transcriptional unit, wherein the transcriptional unit comprises:
   - a sequence encoding a modified Japanese encephalitis virus (JEV) signal sequence comprising SEQ ID NO: 4; and
   - a Zika virus (ZIKV) premembrane (prM) and E protein (prME) coding sequence, wherein the E protein comprises a lysine substitution at position 106 and an aspartic acid substitution at position 107, wherein the numbering is based upon the E protein of ZIKV strain MR766.

2. The vector of claim 1, wherein the transcriptional unit further comprises a promoter operably linked to the prME coding sequence.

3. The vector of claim 2, wherein the promoter comprises the cytomegalovirus (CMV) E1A promoter.

4. The vector of claim 1, wherein the transcriptional unit further comprises a transcription termination sequence.

5. The vector of claim 4, wherein the transcription termination sequence comprises a bovine growth hormone (BGH) transcription termination sequence.

6. The vector of claim 1, wherein the transcriptional unit further comprises a translation initiation sequence.

7. The vector of claim 6, wherein the translation initiation sequence comprises GCCGCCGCCATGG (SEQ ID NO: 8).

8. The vector of claim 1, wherein the ZIKV is a strain selected from MR-766, SPH2015, P6-740, and FSS 13025.

9. The vector of claim 1, wherein the prME coding sequence is codon-optimized for expression in human cells.

10. The vector of claim 1, wherein the ZIKV prME coding sequence is at least 95% identical to nucleotides 1186-3204 of SEQ ID NO: 20 or nucleotides 1186-3210 of SEQ ID NO: 22.

11. The vector of claim 10, wherein the ZIKV prME coding sequence comprises or consists of nucleotides 1186-3204 of SEQ ID NO: 20 or nucleotides 1186-3210 of SEQ ID NO: 22.

12. The vector of claim 1, which is an adenovirus vector.

13. An isolated cell comprising the vector of claim 1.

14. A recombinant adenovirus, comprising a nucleic acid molecule comprising a transcriptional unit, wherein the transcriptional unit comprises:

a sequence encoding a modified Japanese encephalitis virus (JEV) signal sequence comprising SEQ ID NO: 4; and a Zika virus (ZIKV) premembrane (prM) and E protein (prME) coding sequence, wherein the E protein comprises a lysine substitution at position 106 and an aspartic acid substitution at position 107, wherein the numbering is based upon the E protein of ZIKV strain MR766.

15. The recombinant adenovirus of claim 14, wherein the transcriptional unit further comprises:

a promoter operably linked to the prME coding sequence;

a transcription termination sequence; and/or a translation initiation sequence.

16. The recombinant adenovirus of claim 15, wherein:

the promoter comprises the cytomegalovirus (CMV) E1A promoter;

the transcription termination sequence comprises a bovine growth hormone (BGH) transcription termination sequence; and/or the translation initiation sequence comprises GCCGCCGCCATGG (SEQ ID NO: 8).

17. The recombinant adenovirus of claim 14, wherein the ZIKV is a strain selected from MR-766, SPH2015, P6-740 and FSS 13025.

18. The recombinant adenovirus of claim 14, wherein the prME coding sequence is codon-optimized for expression in human cells.

19. The recombinant adenovirus of claim 14, wherein the ZIKV prME coding sequence is at least 95% identical to nucleotides 1186-3204 of SEQ ID NO: 20 or nucleotides 1186-3210 of SEQ ID NO: 22.

20. The recombinant adenovirus of claim 19, wherein the ZIKV prME coding sequence comprises or consists of nucleotides 1186-3204 of SEQ ID NO: 20 or nucleotides 1186-3210 of SEQ ID NO: 22.

* * * * *

```
                        SEQUENCE LISTING

<160> NUMBER OF SEQ ID NOS: 29

<210> SEQ ID NO 1
<211> LENGTH: 5703
<212> TYPE: DNA
<213> ORGANISM: Artificial Sequence
<220> FEATURE:
<223> OTHER INFORMATION: Plasmid construct pEZMRprME1-8

<400> SEQUENCE: 1
ttcctgcgtt atcccctgat tctgtggata accgtattac cgctagcatg gatctcgggg      60
acgtctaact actaagcgag agtagggaac tgccaggcat caaataaaac gaaaggctca     120
gtcggaagac tgggcctttc gttttatctg ttgtttgtcg gtgaacgctc tcctgagtag     180
gacaaatccg ccgggagcgg atttgaacgt tgtgaagcaa cggcccggag ggtggcgggc     240
aggacgcccg ccataaactg ccaggcatca aactaagcag aaggccatcc tgacggatgg     300
cctttttgcg tttctacaaa ctcttcctgt tagttagtta cttaagctcg gcccccaaat     360
aatgatttta tttaactttg tacaaaaaag caggcttcga aggagataga accaattctc     420
```

```
taaggaaata cttaaccatg gtcgactgga tccggtaccg aattcgtcga ctagcccata      480
tatggagttc cgcgttacat aacttacggt aaatggcccg cctggctgac cgcccaacga      540
cccccgccca ttgacgtcaa taatgacgta tgttcccata gtaacgccaa tagggacttt      600
ccattgacgt caatgggtgg agtatttacg gtaaactgcc cacttggcag tacatcaagt      660
gtatcatatg ccaagtacgc ccctattga cgtcaatgac ggtaaatggc ccgcctggca       720
ttatgcccag tacatgacct tatgggactt tcctacttgg cagtacatct acgtattagt      780
catcgctatt accatggtga tgcggttttg gcagtacatc aatgggcgtg gatagcggtt      840
tgactcacgg ggatttccaa gtctccaccc cattgacgtc aatgggagtt tgttttggca      900
ccaaaatcaa cgggactttc caaaatgtcg taacaactcc gccccattga cgcaaatggg      960
cggtaggcgt gtacggtggg aggtctatat aagcagagct ctctggctaa ctagagaacc     1020
cactgcttac tggcttatcg aaattaatac gactcactat agggagaccc aagctggcta     1080
gcgtttaaac ttaagcttgg taccgccgcc gccatgggca agaggtccgc cggctcaatc     1140
atgtggctcg cgagcttggc agttgtcata gctggtacaa gcgctgcaga gatcactaga     1200
cgcgggagtg catactacat gtacttggat aggagcgatg ccgggaaggc catttcgttt     1260
gctaccacat tgggagtgaa caagtgccac gtacagatca tggacctcgg gcacatgtgt     1320
gacgccacca tgagttatga gtgccctatg ctggatgagg agtggaacc agatgatgtc      1380 gattgctggt gcaacacgac atcaacttgg gttgtgtacg aacctgtca tcacaaaaaa      1440 ggtgaggcac ggcgatctag aagagccgtg acgctcccct ctcactctac gaggaagttg     1500
caaacgcggt cgcagacctg gttagaatca agagaataca cgaagcactt gatcaaggtt     1560
gaaaactgga tattcaggaa ccccgggttt gcgctagtgg ccgttgccat tgcctggctt     1620 tgggaagct cgacgagcca aaaagtcata tacttggtca tgatactgct gattgccccg      1680
gcatacagta tcaggtgcat tggagtcagc aatagagact tcgtggaggg catgtcaggt     1740
gggacctggg ttgatgttgt cttggaacat ggaggctgcg ttaccgtgat ggcacaggac     1800
aagccaacag ttgacataga gttggtcacg acgacggtta gtaacatggc cgaggtaaga     1860
tcctattgct acgaggcatc gatatcggac atggcttcgg acagtcgttg cccaacacaa     1920
ggtgaagcct accttgacaa gcaatcagac actcaatatg tctgcaaaag aacattagtg     1980
gacagaggtt ggggaaacgg ttgtggactt tttggcaaag ggagcttggt gacatgtgcc     2040
aagtttacgt gttctaagaa gatgaccggg aagagcattc aaccggaaaa tctggagtat     2100
cggataatgc tatcagtgca tggctcccag catagcggga tgattgtcaa tgatacagga     2160
tatgaaactg acgaaaatag agcgaaagtc gaggttacgc ctaattcacc aagagcggaa     2220
gcaaccttgg gaggctttgg aagcttagga cttgactgtg aaccaaggac aggccttgac     2280
ttttcagatc tgtattacct gaccatgaac aataagcatt ggttggtgca aaagagtgg     2340 tttcatgaca tcccattgcc ttggcatgct ggggcagaca ccggaactcc acactggaac     2400
aacaaagagg cattggtaga attcaaggat gcccacgcca agaggcaaac cgtcgtcgtt     2460
ctggggagcc aggaaggagc cgttcacacg gctctcgctg gagctctaga ggctgagatg     2520
gatggtgcaa agggaaagct gttctctggc catttgaaat gccgcctaaa aatggacaag     2580
cttagattga agggcgtgtc atattccttg tgcactgcgg cattcacatt caccaaggtc     2640
ccagctgaaa cactgcatgg aacagtcaca gtggaggtgc agtatgcagg acagatggga     2700
ccctgcaaga tcccagtcca gatggcggtg gacatgcaga ccctgacccc agttggaggg     2760
```

```
ctgataaccg ccaacccecgt gattactgaa agcactgaga actcaaagat gatgttggag    2820
cttgacccac catttgggga ttcttacatt gtcataggag ttggggacaa gaaaatcacc    2880
caccactggc ataggagtgg tagcaccatc ggaaaggcat ttgaggccac tgtgagaggc    2940
gccaagagaa tggcagtcct gggggataca gcctgggact tcggatcagt cgggggtgtg    3000
ttcaactcac tgggtaaggg cattcaccag atttttggag cagccttcaa atcactgttt    3060
ggaggaatgt cctggttctc acagatcctc ataggcacgc tgctagtgtg gttaggtttg    3120
aacacaaaga atggatctat ctccctcaca tgcttggccc tgggggggagt gatgatcttc    3180
ctctccacgg ctgtttctgc ttgagcggcc gctcgagtct agagggcccg tttaaacccg    3240
ctgatcagcc tcgactgtgc cttctagttg ccagccatct gttgtttgcc cctcccccgt    3300
gccttccttg accctggaag gtgccactcc cactgtcctt tcctaataaa atgaggaaat    3360
tgcatcgcat tgtctgagta ggtgtcattc tattctgggg ggtggggtgg ggcaggacag    3420
caagggggag gattgggaag acaatagcag gcatgctggg gatgcggtgg gctctatggc    3480
ttctactggg cggttttatg gacagcaagc gaaccggaat tgccagctgg ggcgccctct    3540
ggtaaggtga tatctagacc cagctttctt gtacaaagtt ggcattataa gaaagcattg    3600
cttatcaatt tgttgcaacg aacaggtcac tatcagtcaa aataaaatca ttatttgcca    3660
tccagctgca gctctggccc gtgtctcaaa atctctgatg ttacattgca caagataaaa    3720
atatatcatc atgaacaata aaactgtctg cttacataaa cagtaataca aggggtgtta    3780
tgagccatat tcaacgggaa acgtcgaggc cgcgattaaa ttccaacatg gatgctgatt    3840
tatatgggta taaatgggct cgcgataatg tcgggcaatc aggtgcgaca atctatcgct    3900
tgtatgggaa gcccgatgcg ccagagttgt ttctgaaaca tggcaaaggt agcgttgcca    3960
atgatgttac agatgagatg gtcagactaa actggctgac ggaatttatg cctcttccga    4020
ccatcaagca ttttatccgt actcctgatg atgcatggtt actcaccact gcgatccccg    4080
gaaaaacagc attccaggta ttagaagaat atcctgattc aggtgaaaat attgttgatg    4140
cgctggcagt gttcctgcgc cggttgcatt cgattcctgt ttgtaattgt ccttttaaca    4200
gcgatcgcgt atttcgtctc gctcaggcgc aatcacgaat gaataacggt ttggttgatg    4260
cgagtgattt tgatgacgag cgtaatggct ggcctgttga acaagtctgg aaagaaatgc    4320
ataaactttt gccattctca ccggattcag tcgtcactca tggtgatttc tcacttgata    4380
accttatttt tgacgagggg aaattaatag gttgtattga tgttggacga gtcggaatcg    4440
cagaccgata ccaggatctt gccatcctat ggaactgcct cggtgagttt tctccttcat    4500
tacagaaacg ctttttcaa aaatatggta ttgataatcc tgatatgaat aaattgcagt    4560
ttcatttgat gctcgatgag ttttttctaat cagaattggt taattggttg taacattatt    4620
cagattgggc cccgttccac tgagcgtcag accccgtaga aaagatcaaa ggatcttctt    4680
gagatccttt ttttctgcgc gtaatctgct gcttgcaaac aaaaaaacca ccgctaccag    4740
cggtggtttg tttgccggat caagagctac caactctttt tccgaaggta actggcttca    4800
gcagagcgca gataccaaat actgttcttc tagtgtagcc gtagttaggc caccacttca    4860
agaactctgt agcaccgcct acatacccg ctctgctaat cctgttacca gtggctgctg    4920
ccagtggcga taagtcgtgt cttaccgggt tggactcaag acgatagtta ccggataagg    4980
cgcagcggtc gggctgaacg gggggttcgt gcacacagcc cagcttggag cgaacgacct    5040
acaccgaact gagatacta cagcgtgagc tatgagaaag cgccacgctt cccgaaggga    5100
gaaaggcgga caggtatccg gtaagcggca gggtcggaac aggagagcgc acgagggagc    5160
```

```
ttccaggggg aaacgcctgg tatctttata gtcctgtcgg gtttcgccac ctctgacttg    5220
agcgtcgatt tttgtgatgc tcgtcagggg ggcggagcct atggaaaaac gccagcaacg    5280
cggccttttt acggttcctg gccttttgct ggccttttgc tcacatgttc tttcctgcgt    5340
tatcccctga ttctgtggat aaccgtatta ccgctagcat ggatctcggg gacgtctaac    5400
tactaagcga gagtagggaa ctgccaggca tcaaataaaa cgaaaggctc agtcggaaga    5460
ctgggccttt cgttttatct gttgtttgtc ggtgaacgct ctcctgagta ggacaaatcc    5520
gccgggagcg gatttgaacg ttgtgaagca acggcccgga gggtggcggg caggacgccc    5580
gccataaact gccaggcatc aaactaagca gaaggccatc ctgacggatg ccttttttgc    5640
gtttctacaa actcttcctg ttagttagtt acttaagctc gggccccaaa taatgatttt    5700
att                                                                  5703

<210> SEQ ID NO 2
<211> LENGTH: 5712
<212> TYPE: DNA
<213> ORGANISM: Artificial Sequence
<220> FEATURE:
<223> OTHER INFORMATION: Plasmid construct pEBZHu8

<400> SEQUENCE: 2
ttcctgcgtt atcccctgat tctgtggata accgtattac cgctagcatg gatctcgggg      60
acgtctaact actaagcgag agtagggaac tgccaggcat caaataaaac gaaaggctca     120
gtcggaagac tgggcctttc gttttatctg ttgtttgtcg gtgaacgctc tcctgagtag     180
gacaaatccg ccgggagcgg atttgaacgt tgtgaagcaa cggcccggag ggtggcgggc     240
aggacgcccg ccataaactg ccaggcatca aactaagcag aaggccatcc tgacggatgg     300 ccttttttgcg tttctacaaa ctcttcctgt tagttagtta cttaagctcg gccccaaat     360 aatgatttta tttaactttg tacaaaaaag caggcttcga aggagataga accaattctc     420
taaggaaata cttaaccatg gtcgactgga tccggtaccg aattcgtcga ctagcccata     480
tatggagttc cgcgttacat aacttacggt aaatggcccg cctggctgac cgcccaacga     540
cccccgccca ttgacgtcaa taatgacgta tgttcccata gtaacgccaa tagggacttt     600
ccattgacgt caatgggtgg agtatttacg gtaaactgcc cacttggcag tacatcaagt     660
gtatcatatg ccaagtacgc cccctattga cgtcaatgac ggtaaatggc ccgcctggca     720
ttatgcccag tacatgacct tatgggactt tcctacttgg cagtacatct acgtattagt     780
catcgctatt accatggtga tgcggttttg gcagtacatc aatgggcgtg atagcggtt     840 tgactcacgg ggatttccaa gtctccaccc cattgacgtc aatgggagtt tgttttggca     900
ccaaaatcaa cgggactttc caaaatgtcg taacaactcc gccccattga cgcaaatggg     960
cggtaggcgt gtacggtggg aggtctatat aagcagagct ctctggctaa ctagagaacc    1020
cactgcttac tggcttatcg aaattaatac gactcactat agggagaccc aagctggcta    1080
gcgtttaaac ttaagcttgg taccgccgcc gccatgggca gaggtccgc ggctcaatc      1140 atgtggctcg cgagcttggc agttgtcata gctggtacaa gcgctgccgt ggaagtgacc    1200
agaagaggca gcgcctacta catgtacctg accggaacg atgccggcga ggccatcagc    1260
tttccaacca ccctgggcat gaacaagtgc tacatccaga tcatggacct gggccacatg    1320
tgcgacgcca ccatgagcta cgagtgcccc atgctggacg agggcgtgga accgacgat    1380 gtggactgct ggtgcaacac caccagcacc tgggtggtgt acggcacctg tcaccacaag    1440
```

```
aagggcgaag ccagacggtc cagacgggcc gtgacactgc ctagccacag caccagaaag    1500
ctgcagaccc ggtcccagac ctggctggaa agcagagagt acaccaagca cctgatccgg    1560
gtggaaaact ggatcttccg gaaccccggc tttgccctgg ccgctgctgc tattgcttgg    1620
ctgctgggca gcagcacctc ccagaaagtg atctacctcg tgatgatcct gctgatcgcc    1680
cctgcctaca gcatccggtg tatcggcgtg tccaaccggg acttcgtgga aggcatgagc    1740
ggcggcacat gggtggacat cgtgctgaaa cacggcggct gcgtgacagt gatggcccag    1800
gataagccca ccgtggacat tgagctcgtg accaccaccg tgtccaatat ggccgaagtg    1860
cggagctact gctacgaggc cagcatcagc gacatggcca gcgacagcag atgccccaca    1920
cagggcgagg cttacctgga caagcagtcc gacacccagt acgtgtgcaa gcggaccctg    1980
gtggatagag gctggggcaa tggctgcggc ctgtttggca agggcagcct cgtgacctgc    2040
gccaagttcg cctgcagcaa gaagatgacc ggcaagagca tccagcccga gaacctggaa    2100
taccggatca tgctgagcgt gcacggcagc cagcactccg gcatgatcgt gaacgacacc    2160
ggccacgaga cagacgagaa ccgggccaag gtggaaatca cccccaacag ccctagagcc    2220
gaggccacac tgggcggctt tggatctctg ggcctggact gcgagcctag aaccggcctg    2280
gatttcagcg acctgtacta cctgaccatg aacaacaagc actggctggt gcacaaagag    2340
tggttccacg acatccccct gccctggcat gccggcgctg atacaggcac accccactgg    2400
aacaacaaag aggctctggt ggagttcaag gacgcccacg ccaagaggca gaccgtggtg    2460
gtgctgggat ctcaggaagg cgccgtgcat acagctctgg ctggcgccct ggaagccgaa    2520
atggatggcg ctaagggcag actgtccagc ggccacctga gtgccggct gaagatggac    2580 aagctgcggc tgaagggcgt gtcctacagc ctgtgtaccg ccgccttcac cttcaccaag    2640
atccccgccg agacactgca cggcaccgtg actgtggaag tgcagtacgc cggcaccgac    2700
ggcccttgta aagtgcctgc tcagatggcc gtggatatgc agaccctgac ccctgtgggc    2760
aggctgatca ccgccaaccc tgtgatcacc gagagcaccg agaacagcaa gatgatgctg    2820
gaactggacc cccccttcgg cgactcctac atcgtgatcg gcgtgggaga agaagaagatc    2880 acccaccact ggcacagaag cggcagcacc atcggcaaag ccttcgaagc cacagtgcgg    2940
ggagccaaga gaatggccgt gctgggagat accgcctggg actttggctc tgtgggcgga    3000
gccctgaact ctctgggcaa gggaatccac cagatcttcg gagccgcctt taagagcctg    3060
ttcggcggca tgagctggtt cagccagatc ctgatcggca ccctgctgat gtggctgggc    3120
ctgaacacca gaacggcag catctccctg atgtgcctgg ctctgggagg cgtgctgatc    3180
ttcctgagca cagccgtgtc tgccgacgtg tgagcggccg ctcgagtcta gagggcccgt    3240
ttaaacccgc tgatcagcct cgactgtgcc ttctagttgc cagccatctg ttgtttgccc    3300 ctccccgtg ccttccttga ccctggaagg tgccactccc actgtccttt cctaataaaa    3360
tgaggaaatt gcatcgcatt gtctgagtag gtgtcattct attctggggg gtggggtggg    3420
gcaggacagc aagggggagg attgggaaga caatagcagg catgctgggg atgcggtggg    3480
ctctatggct tctactgggc ggttttatgg acagcaagcg aaccggaatt gccagctggg    3540
gcgccctctg gtaaggtgat atctagaccc agctttcttg tacaaagttg gcattataag    3600
aaagcattgc ttatcaattt gttgcaacga acaggtcact atcagtcaaa ataaaatcat    3660
tatttgccat ccagctgcag ctctggcccg tgtctcaaaa tctctgatgt tacattgcac    3720
aagataaaaa tatatcatca tgaacaataa aactgtctgc ttacataaac agtaatacaa    3780
ggggtgttat gagccatatt caacgggaaa cgtcgaggcc gcgattaaat tccaacatgg    3840
```

| | |
|---|---|
| atgctgattt atatgggtat aaatgggctc gcgataatgt cgggcaatca ggtgcgacaa | 3900 |
| tctatcgctt gtatgggaag cccgatgcgc cagagttgtt tctgaaacat ggcaaaggta | 3960 |
| gcgttgccaa tgatgttaca gatgagatgg tcagactaaa ctggctgacg gaatttatgc | 4020 |
| ctcttccgac catcaagcat tttatccgta ctcctgatga tgcatggtta ctcaccactg | 4080 |
| cgatccccgg aaaaacagca ttccaggtat tagaagaata tcctgattca ggtgaaaata | 4140 |
| ttgttgatgc gctggcagtg ttcctgcgcc ggttgcattc gattcctgtt tgtaattgtc | 4200 |
| cttttaacag cgatcgcgta tttcgtctcg ctcaggcgca atcacgaatg aataacggtt | 4260 |
| tggttgatgc gagtgatttt gatgacgagc gtaatggctg gcctgttgaa caagtctgga | 4320 |
| aagaaatgca taaacttttg ccattctcac cggattcagt cgtcactcat ggtgatttct | 4380 |
| cacttgataa ccttattttt gacgagggga aattaatagg ttgtattgat gttggacgag | 4440 |
| tcggaatcgc agaccgatac caggatcttg ccatcctatg gaactgcctc ggtgagtttt | 4500 |
| ctccttcatt acagaaacgg cttttttcaaa atatggtat tgataatcct gatatgaata | 4560 |
| aattgcagtt tcatttgatg ctcgatgagt ttttctaatc agaattggtt aattggttgt | 4620 |
| aacattattc agattgggcc ccgttccact gagcgtcaga ccccgtagaa aagatcaaag | 4680 |
| gatcttcttg agatcctttt tttctgcgcg taatctgctg cttgcaaaca aaaaaaccac | 4740 |
| cgctaccagc ggtggtttgt ttgccggatc aagagctacc aactctttt ccgaaggtaa | 4800 |
| ctggcttcag cagagcgcag ataccaaata ctgttcttct agtgtagccg tagttaggcc | 4860 |
| accacttcaa gaactctgta gcaccgccta catacctcgc tctgctaatc ctgttaccag | 4920 |
| tggctgctgc cagtggcgat aagtcgtgtc ttaccgggtt ggactcaaga cgatagttac | 4980 |
| cggataaggc gcagcggtcg ggctgaacgg ggggttcgtg cacacagccc agcttggagc | 5040 |
| gaacgaccta caccgaactg agatacctac agcgtgagct atgagaaagc gccacgcttc | 5100 |
| ccgaagggag aaaggcggac aggtatccgg taagcggcag ggtcggaaca ggagagcgca | 5160 |
| cgagggagct tccaggggga aacgcctggt atctttatag tcctgtcggg tttcgccacc | 5220 |
| tctgacttga gcgtcgattt ttgtgatgct cgtcaggggg gcggagccta tggaaaaacg | 5280 |
| ccagcaacgc ggccttttta cggttcctgg ccttttgctg ccttttgct cacatgttct | 5340 |
| ttcctgcgtt atcccctgat tctgtggata accgtattac cgctagcatg gatctcgggg | 5400 |
| acgtctaact actaagcgag agtagggaac tgccaggcat caaataaaac gaaaggctca | 5460 |
| gtcggaagac tgggcctttc gttttatctg ttgtttgtcg gtgaacgctc tcctgagtag | 5520 |
| gacaaatccg ccgggagcgg atttgaacgt tgtgaagcaa cggcccggag ggtggcgggc | 5580 |
| aggacgcccg ccataaactg ccaggcatca aactaagcag aaggccatcc tgacggatgg | 5640 |
| cctttttgcg tttctacaaa ctcttcctgt tagttagtta cttaagctcg ggccccaaat | 5700 |
| aatgatttta tt | 5712 |

<210> SEQ ID NO 3
<211> LENGTH: 5709
<212> TYPE: DNA
<213> ORGANISM: Artificial Sequence
<220> FEATURE:
<223> OTHER INFORMATION: Plasmid construct pEBZHu2-3

<400> SEQUENCE: 3

| | |
|---|---|
| ttcctgcgtt atcccctgat tctgtggata accgtattac cgctagcatg gatctcgggg | 60 |
| acgtctaact actaagcgag agtagggaac tgccaggcat caaataaaac gaaaggctca | 120 |

```
gtcggaagac tgggcctttc gttttatctg ttgtttgtcg gtgaacgctc tcctgagtag      180
gacaaatccg ccgggagcgg atttgaacgt tgtgaagcaa cggcccggag ggtggcgggc      240
aggacgcccg ccataaactg ccaggcatca aactaagcag aaggccatcc tgacggatgg      300
cctttttgcg tttctacaaa ctcttcctgt tagttagtta cttaagctcg gcccccaaat      360
aatgatttta tttaactttg tacaaaaaag caggcttcga aggagataga accaattctc      420
taaggaaata cttaaccatg gtcgactgga tccggtaccg aattcgtcga ctagcccata      480
tatggagttc cgcgttacat aacttacggt aaatggcccg cctggctgac cgcccaacga      540
cccccgccca ttgacgtcaa taatgacgta tgttcccata gtaacgccaa tagggacttt      600
ccattgacgt caatgggtgg agtatttacg gtaaactgcc cacttggcag tacatcaagt      660
gtatcatatg ccaagtacgc ccctattga cgtcaatgac ggtaaatggc ccgcctggca      720
ttatgcccag tacatgacct tatgggactt tcctacttgg cagtacatct acgtattagt      780
catcgctatt accatggtga tgcggttttg gcagtacatc aatgggcgtg gatagcggtt      840
tgactcacgg ggatttccaa gtctccaccc cattgacgtc aatgggagtt tgttttggca      900
ccaaaatcaa cgggactttc caaaatgtcg taacaactcc gccccattga cgcaaatggg      960
cggtaggcgt gtacggtggg aggtctatat aagcagagct ctctggctaa ctagagaacc     1020
cactgcttac tggcttatcg aaattaatac gactcactat agggagaccc aagctggcta     1080
gcgtttaaac ttaagcttgg taccgccgcc gccatgggca agaggtccgc cggctcaatc     1140
atgtggctcg cgagcttggc agttgtcata gctggtacaa gcgccgtgga agtgaccaga     1200
agaggcagcg cctactacat gtacctggac cggaacgatg ccggcgaggc catcagcttt     1260
ccaaccaccc tgggcatgaa caagtgctac atccagatca tggacctggg ccacatgtgc     1320
gacgccacca tgagctacga gtgccccatg ctggacgagg gcgtggaacc cgacgatgtg     1380
gactgctggt gcaacaccac cagcacctgg gtggtgtacg gcacctgtca ccacaagaag     1440
ggcgaagcca cacggtccag acgggccgtg acactgccta ccacagcac cagaaagctg     1500 cagacccggt cccagacctg gctggaaagc agagagtaca ccaagcacct gatccgggtg     1560
gaaaactgga tcttccggaa ccccggcttt gccctggccg ctgctgctat tgcttggctg     1620
ctgggcagca gcacctccca gaaagtgatc tacctcgtga tgatcctgct gatcgcccct     1680
gcctacagca tccggtgtat cggcgtgtcc aacggggact tcgtggaagg catgagcggc     1740
ggcacatggg tggacatcgt gctggaacac ggcggctgcg tgacagtgat ggcccaggat     1800
aagcccaccg tggacattga gctcgtgacc accaccgtgt ccaatatggc cgaagtgcgg     1860
agctactgct acgaggccag catcagcgac atggccagcg acagcagatg ccccacacag     1920
ggcgaggctt acctggacaa gcagtccgac acccagtacg tgtgcaagcg gaccctggtg     1980
gatagaggct ggggcaatgg ctgcggcctg tttggcaagg gcagcctcgt gacctgcgcc     2040
aagttcgcct gcagcaagaa gatgaccggc aagagcatcc agcccgagaa cctggaatac     2100
cggatcatgc tgagcgtgca cggcagccag cactccggca tgatcgtgaa cgacaccggc     2160
cacgagacag acgagaaccg ggccaaggtg gaaatcaccc ccaacagccc tagagccgag     2220
gccacactgg gcggctttgg atctctgggc ctggactgcg agcctagaac cggcctggat     2280
ttcagcgacc tgtactacct gaccatgaac aacaagcact ggctggtgca caaagagtgg     2340
ttccacgaca tccccctgcc ctggcatgcc ggcgctgata caggcacacc ccactggaac     2400
aacaaagagg ctctggtgga gttcaaggac gcccacgcca gaggcagac cgtggtggtg     2460 ctgggatctc aggaaggcgc cgtgcataca gctctggctg gcgccctgga agccgaaatg     2520
```

```
gatggcgcta agggcagact gtccagcggc cacctgaagt gccggctgaa gatggacaag    2580
ctgcggctga agggcgtgtc ctacagcctg tgtaccgccg ccttcacctt caccaagatc    2640
cccgccgaga cactgcacgg caccgtgact gtggaagtgc agtacgccgg caccgacggc    2700
ccttgtaaag tgcctgctca gatggccgtg gatatgcaga ccctgacccc tgtgggcagg    2760
ctgatcaccg ccaaccctgt gatcaccgag agcaccgaga cagcaagat gatgctggaa     2820 ctggaccccc ccttcggcga ctcctacatc gtgatcggcg tgggagagaa gaagatcacc    2880
caccactggc acagaagcgg cagcaccatc ggcaaagcct tcgaagccac agtgcgggga    2940
gccaagagaa tggccgtgct gggagatacc gcctgggact tggctctgt gggcggagcc     3000 ctgaactctc tgggcaaggg aatccaccag atcttcggag ccgcctttaa gagcctgttc    3060
ggcggcatga gctggttcag ccagatcctg atcggcaccc tgctgatgtg gctgggcctg    3120
aacaccaaga acggcagcat ctccctgatg tgcctggctc tgggaggcgt gctgatcttc    3180
ctgagcacag ccgtgtctgc cgacgtgtga gcggccgctc gagtctagag ggcccgttta   3240
aacccgctga tcagcctcga ctgtgccttc tagttgccag ccatctgttg tttgcccctc    3300
ccccgtgcct tccttgaccc tggaaggtgc cactcccact gtcctttcct aataaaatga    3360
ggaaattgca tcgcattgtc tgagtaggtg tcattctatt ctggggggtg gggtggggca    3420
ggacagcaag ggggaggatt gggaagacaa tagcaggcat gctggggatg cggtgggctc    3480
tatggcttct actgggcggt tttatggaca gcaagcgaac cggaattgcc agctggggcg    3540
ccctctggta aggtgatatc tagacccagc tttcttgtac aaagttggca ttataagaaa    3600
gcattgctta tcaatttgtt gcaacgaaca ggtcactatc agtcaaaata aaatcattat    3660
ttgccatcca gctgcagctc tggcccgtgt ctcaaaatct ctgatgttac attgcacaag    3720
ataaaaatat atcatcatga acaataaaac tgtctgctta cataaacagt aatacaaggg    3780
gtgttatgag ccatattcaa cgggaaacgt cgaggccgcg attaaattcc aacatggatg    3840
ctgatttata tgggtataaa tgggctcgcg ataatgtcgg gcaatcaggt gcgacaatct    3900
atcgcttgta tgggaagccc gatgcgccag agttgtttct gaaacatggc aaaggtagcg    3960
ttgccaatga tgttacagat gagatggtca gactaaactg gctgacggaa tttatgcctc    4020
ttccgaccat caagcatttt atccgtactc ctgatgatgc atggttactc accactgcga    4080
tccccggaaa aacagcattc caggtattag aagaatatcc tgattcaggt gaaaatattg    4140
ttgatgcgct ggcagtgttc ctgcgccggt tgcattcgat tcctgtttgt aattgtcctt    4200
ttaacagcga tcgcgtattt cgtctcgctc aggcgcaatc acgaatgaat aacggtttgg    4260
ttgatgcgag tgattttgat gacgagcgta atggctggcc tgttgaacaa gtctggaaag    4320
aaatgcataa acttttgcca ttctcaccgg attcagtcgt cactcatggt gatttctcac    4380
ttgataacct tattttgac gaggggaaat taataggttg tattgatgtt ggacgagtcg     4440
gaatcgcaga ccgataccag gatcttgcca tcctatggaa ctgcctcggt gagttttctc    4500
cttcattaca gaaacggctt tttcaaaaat atggtattga taatcctgat atgaataaat    4560
tgcagtttca tttgatgctc gatgagtttt tctaatcaga attggttaat ggttgtaac    4620 attattcaga ttgggccccg ttccactgag cgtcagaccc cgtagaaaag atcaaaggat    4680
cttcttgaga tccttttttt ctgcgcgtaa tctgctgctt gcaaacaaaa aaaccaccgc    4740
taccagcggt ggtttgtttg ccggatcaag agctaccaac tctttttccg aaggtaactg    4800
gcttcagcag agcgcagata ccaaatactg ttcttctagt gtagccgtag ttaggccacc    4860
```

-continued

```
acttcaagaa ctctgtagca ccgcctacat acctcgctct gctaatcctg ttaccagtgg   4920
ctgctgccag tggcgataag tcgtgtctta ccgggttgga ctcaagacga tagttaccgg   4980
ataaggcgca gcggtcgggc tgaacggggg gttcgtgcac acagcccagc ttggagcgaa   5040
cgacctacac cgaactgaga tacctacagc gtgagctatg agaaagcgcc acgcttcccg   5100
aagggagaaa ggcggacagg tatccggtaa gcggcagggt cggaacagga gagcgcacga   5160
gggagcttcc agggggaaac gcctggtatc tttatagtcc tgtcgggttt cgccacctct   5220
gacttgagcg tcgatttttg tgatgctcgt caggggggcg gagcctatgg aaaaacgcca   5280
gcaacgcggc ctttttacgg ttcctggcct tttgctggcc ttttgctcac atgttctttc   5340
ctgcgttatc ccctgattct gtggataacc gtattaccgc tagcatggat ctcggggacg   5400
tctaactact aagcgagagt agggaactgc caggcatcaa ataaaacgaa aggctcagtc   5460
ggaagactgg gcctttcgtt ttatctgttg tttgtcggtg aacgctctcc tgagtaggac   5520
aaatccgccg ggagcggatt tgaacgttgt gaagcaacgg cccggagggt ggcgggcagg   5580
acgcccgcca taaactgcca ggcatcaaac taagcagaag gccatcctga cggatggcct   5640
ttttgcgttt ctacaaactc ttcctgttag ttagttactt aagctcgggc cccaaataat   5700
gattttatt                                                           5709

<210> SEQ ID NO 4
<211> LENGTH: 24
<212> TYPE: PRT
<213> ORGANISM: Artificial Sequence
<220> FEATURE:
<223> OTHER INFORMATION: Modified JEV signal sequence

<400> SEQUENCE: 4

Met Gly Lys Arg Ser Ala Gly Ser Ile Met Trp Leu Ala Ser Leu Ala
1               5                   10                  15

Val Val Ile Ala Gly Thr Ser Ala
            20

<210> SEQ ID NO 5
<211> LENGTH: 672
<212> TYPE: PRT
<213> ORGANISM: Artificial Sequence
<220> FEATURE:
<223> OTHER INFORMATION: prME protein expressed by pEZMRprME1-8

<400> SEQUENCE: 5

Ala Glu Ile Thr Arg Arg Gly Ser Ala Tyr Tyr Met Tyr Leu Asp Arg
1               5                   10                  15

Ser Asp Ala Gly Lys Ala Ile Ser Phe Ala Thr Thr Leu Gly Val Asn
            20                  25                  30

Lys Cys His Val Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Lys Val Glu Asn Trp
        115                 120                 125
```

```
Ile Phe Arg Asn Pro Gly Phe Ala Leu Val Ala Val Ala Ile Ala Trp
130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser Ile Arg Cys Ile Gly Val Ser Asn
                165                 170                 175

Arg Asp Phe Val Glu Gly Met Ser Gly Gly Thr Trp Val Asp Val Val
                180                 185                 190

Leu Glu His Gly Gly Cys Val Thr Val Met Ala Gln Asp Lys Pro Thr
            195                 200                 205

Val Asp Ile Glu Leu Val Thr Thr Thr Val Ser Asn Met Ala Glu Val
210                 215                 220

Arg Ser Tyr Cys Tyr Glu Ala Ser Ile Ser Asp Met Ala Ser Asp Ser
225                 230                 235                 240

Arg Cys Pro Thr Gln Gly Glu Ala Tyr Leu Asp Lys Gln Ser Asp Thr
                245                 250                 255

Gln Tyr Val Cys Lys Arg Thr Leu Val Asp Arg Gly Trp Gly Asn Gly
                260                 265                 270

Cys Gly Leu Phe Gly Lys Gly Ser Leu Val Thr Cys Ala Lys Phe Thr
            275                 280                 285

Cys Ser Lys Lys Met Thr Gly Lys Ser Ile Gln Pro Glu Asn Leu Glu
290                 295                 300

Tyr Arg Ile Met Leu Ser Val His Gly Ser Gln His Ser Gly Met Ile
305                 310                 315                 320

Val Asn Asp Thr Gly Tyr Glu Thr Asp Glu Asn Arg Ala Lys Val Glu
                325                 330                 335

Val Thr Pro Asn Ser Pro Arg Ala Glu Ala Thr Leu Gly Gly Phe Gly
                340                 345                 350

Ser Leu Gly Leu Asp Cys Glu Pro Arg Thr Gly Leu Asp Phe Ser Asp
            355                 360                 365

Leu Tyr Tyr Leu Thr Met Asn Asn Lys His Trp Leu Val His Lys Glu
370                 375                 380

Trp Phe His Asp Ile Pro Leu Pro Trp His Ala Gly Ala Asp Thr Gly
385                 390                 395                 400

Thr Pro His Trp Asn Asn Lys Glu Ala Leu Val Glu Phe Lys Asp Ala
                405                 410                 415

His Ala Lys Arg Gln Thr Val Val Leu Gly Ser Gln Glu Gly Ala
                420                 425                 430

Val His Thr Ala Leu Ala Gly Ala Leu Glu Ala Glu Met Asp Gly Ala
            435                 440                 445

Lys Gly Lys Leu Phe Ser Gly His Leu Lys Cys Arg Leu Lys Met Asp
450                 455                 460

Lys Leu Arg Leu Lys Gly Val Ser Tyr Ser Leu Cys Thr Ala Ala Phe
465                 470                 475                 480

Thr Phe Thr Lys Val Pro Ala Glu Thr Leu His Gly Thr Val Thr Val
                485                 490                 495

Glu Val Gln Tyr Ala Gly Thr Asp Gly Pro Cys Lys Ile Pro Val Gln
                500                 505                 510

Met Ala Val Asp Met Gln Thr Leu Thr Pro Val Gly Gly Leu Ile Thr
            515                 520                 525

Ala Asn Pro Val Ile Thr Glu Ser Thr Glu Asn Ser Lys Met Met Leu
530                 535                 540
```

-continued

```
Glu Leu Asp Pro Pro Phe Gly Asp Ser Tyr Ile Val Ile Gly Val Gly
545                 550                 555                 560

Asp Lys Lys Ile Thr His His Trp His Arg Ser Gly Ser Thr Ile Gly
            565                 570                 575

Lys Ala Phe Glu Ala Thr Val Arg Gly Ala Lys Arg Met Ala Val Leu
        580                 585                 590

Gly Asp Thr Ala Trp Asp Phe Gly Ser Val Gly Gly Val Phe Asn Ser
    595                 600                 605

Leu Gly Lys Gly Ile His Gln Ile Phe Gly Ala Ala Phe Lys Ser Leu
610                 615                 620

Phe Gly Gly Met Ser Trp Phe Ser Gln Ile Leu Ile Gly Thr Leu Leu
625                 630                 635                 640

Val Trp Leu Gly Leu Asn Thr Lys Asn Gly Ser Ile Ser Leu Thr Cys
                645                 650                 655

Leu Ala Leu Gly Gly Val Met Ile Phe Leu Ser Thr Ala Val Ser Ala
                660                 665                 670
```

<210> SEQ ID NO 6
<211> LENGTH: 675
<212> TYPE: PRT
<213> ORGANISM: Artificial Sequence
<220> FEATURE:
<223> OTHER INFORMATION: prME protein expressed by pEBZHu8

<400> SEQUENCE: 6

```
Ala Val Glu Val Thr Arg Arg Gly Ser Ala Tyr Tyr Met Tyr Leu Asp
1               5                   10                  15

Arg Asn Asp Ala Gly Glu Ala Ile Ser Phe Pro Thr Thr Leu Gly Met
            20                  25                  30

Asn Lys Cys Tyr Ile Gln Ile Met Asp Leu Gly His Met Cys Asp Ala
        35                  40                  45

Thr Met Ser Tyr Glu Cys Pro Met Leu Asp Glu Gly Val Glu Pro Asp
    50                  55                  60

Asp Val Asp Cys Trp Cys Asn Thr Thr Ser Thr Trp Val Val Tyr Gly
65                  70                  75                  80

Thr Cys His His Lys Lys Gly Glu Ala Arg Arg Ser Arg Arg Ala Val
                85                  90                  95

Thr Leu Pro Ser His Ser Thr Arg Lys Leu Gln Thr Arg Ser Gln Thr
            100                 105                 110

Trp Leu Glu Ser Arg Glu Tyr Thr Lys His Leu Ile Arg Val Glu Asn
        115                 120                 125

Trp Ile Phe Arg Asn Pro Gly Phe Ala Leu Ala Ala Ala Ala Ile Ala
    130                 135                 140

Trp Leu Leu Gly Ser Ser Thr Ser Gln Lys Val Ile Tyr Leu Val Met
145                 150                 155                 160

Ile Leu Leu Ile Ala Pro Ala Tyr Ser Ile Arg Cys Ile Gly Val Ser
                165                 170                 175

Asn Arg Asp Phe Val Glu Gly Met Ser Gly Gly Thr Trp Val Asp Ile
            180                 185                 190

Val Leu Glu His Gly Gly Cys Val Thr Val Met Ala Gln Asp Lys Pro
        195                 200                 205

Thr Val Asp Ile Glu Leu Val Thr Thr Thr Val Ser Asn Met Ala Glu
    210                 215                 220

Val Arg Ser Tyr Cys Tyr Glu Ala Ser Ile Ser Asp Met Ala Ser Asp
225                 230                 235                 240
```

```
Ser Arg Cys Pro Thr Gln Gly Glu Ala Tyr Leu Asp Lys Gln Ser Asp
                245                 250                 255

Thr Gln Tyr Val Cys Lys Arg Thr Leu Val Asp Arg Gly Trp Gly Asn
            260                 265                 270

Gly Cys Gly Leu Phe Gly Lys Gly Ser Leu Val Thr Cys Ala Lys Phe
        275                 280                 285

Ala Cys Ser Lys Lys Met Thr Gly Lys Ser Ile Gln Pro Glu Asn Leu
    290                 295                 300

Glu Tyr Arg Ile Met Leu Ser Val His Gly Ser Gln His Ser Gly Met
305                 310                 315                 320

Ile Val Asn Asp Thr Gly His Glu Thr Asp Glu Asn Arg Ala Lys Val
                325                 330                 335

Glu Ile Thr Pro Asn Ser Pro Arg Ala Glu Ala Thr Leu Gly Gly Phe
            340                 345                 350

Gly Ser Leu Gly Leu Asp Cys Glu Pro Arg Thr Gly Leu Asp Phe Ser
        355                 360                 365

Asp Leu Tyr Tyr Leu Thr Met Asn Asn Lys His Trp Leu Val His Lys
    370                 375                 380

Glu Trp Phe His Asp Ile Pro Leu Pro Trp His Ala Gly Ala Asp Thr
385                 390                 395                 400

Gly Thr Pro His Trp Asn Asn Lys Glu Ala Leu Val Glu Phe Lys Asp
                405                 410                 415

Ala His Ala Lys Arg Gln Thr Val Val Leu Gly Ser Gln Glu Gly
            420                 425                 430

Ala Val His Thr Ala Leu Ala Gly Ala Leu Glu Ala Glu Met Asp Gly
        435                 440                 445

Ala Lys Gly Arg Leu Ser Ser Gly His Leu Lys Cys Arg Leu Lys Met
    450                 455                 460

Asp Lys Leu Arg Leu Lys Gly Val Ser Tyr Ser Leu Cys Thr Ala Ala
465                 470                 475                 480

Phe Thr Phe Thr Lys Ile Pro Ala Glu Thr Leu His Gly Thr Val Thr
                485                 490                 495

Val Glu Val Gln Tyr Ala Gly Thr Asp Gly Pro Cys Lys Val Pro Ala
            500                 505                 510

Gln Met Ala Val Asp Met Gln Thr Leu Thr Pro Val Gly Arg Leu Ile
        515                 520                 525

Thr Ala Asn Pro Val Ile Thr Glu Ser Thr Glu Asn Ser Lys Met Met
    530                 535                 540

Leu Glu Leu Asp Pro Pro Phe Gly Asp Ser Tyr Ile Val Ile Gly Val
545                 550                 555                 560

Gly Glu Lys Lys Ile Thr His His Trp His Arg Ser Gly Ser Thr Ile
                565                 570                 575

Gly Lys Ala Phe Glu Ala Thr Val Arg Gly Ala Lys Arg Met Ala Val
            580                 585                 590

Leu Gly Asp Thr Ala Trp Asp Phe Gly Ser Val Gly Gly Ala Leu Asn
        595                 600                 605

Ser Leu Gly Lys Gly Ile His Gln Ile Phe Gly Ala Ala Phe Lys Ser
    610                 615                 620

Leu Phe Gly Gly Met Ser Trp Phe Ser Gln Ile Leu Ile Gly Thr Leu
625                 630                 635                 640

Leu Met Trp Leu Gly Leu Asn Thr Lys Asn Gly Ser Ile Ser Leu Met
                645                 650                 655

Cys Leu Ala Leu Gly Gly Val Leu Ile Phe Leu Ser Thr Ala Val Ser
```

```
                    660                 665                 670
Ala Asp Val
        675

<210> SEQ ID NO 7
<211> LENGTH: 674
<212> TYPE: PRT
<213> ORGANISM: Artificial Sequence
<220> FEATURE:
<223> OTHER INFORMATION: prME protein expressed by pEBZHu2-3

<400> SEQUENCE: 7

Val Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Arg Val Glu Asn Trp
        115                 120                 125

Ile Phe Arg Asn Pro Gly Phe Ala Leu Ala Ala Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser Ile Arg Cys Ile Gly Val Ser Asn
                165                 170                 175

Arg Asp Phe Val Glu Gly Met Ser Gly Gly Thr Trp Val Asp Ile Val
            180                 185                 190

Leu Glu His Gly Gly Cys Val Thr Val Met Ala Gln Asp Lys Pro Thr
        195                 200                 205

Val Asp Ile Glu Leu Val Thr Thr Val Ser Asn Met Ala Glu Val
    210                 215                 220

Arg Ser Tyr Cys Tyr Glu Ala Ser Ile Ser Asp Met Ala Ser Asp Ser
225                 230                 235                 240

Arg Cys Pro Thr Gln Gly Glu Ala Tyr Leu Asp Lys Gln Ser Asp Thr
                245                 250                 255

Gln Tyr Val Cys Lys Arg Thr Leu Val Asp Arg Gly Trp Gly Asn Gly
            260                 265                 270

Cys Gly Leu Phe Gly Lys Gly Ser Leu Val Thr Cys Ala Lys Phe Ala
        275                 280                 285

Cys Ser Lys Lys Met Thr Gly Lys Ser Ile Gln Pro Glu Asn Leu Glu
    290                 295                 300

Tyr Arg Ile Met Leu Ser Val His Gly Ser Gln His Ser Gly Met Ile
305                 310                 315                 320

Val Asn Asp Thr Gly His Glu Thr Asp Glu Asn Arg Ala Lys Val Glu
                325                 330                 335

Ile Thr Pro Asn Ser Pro Arg Ala Glu Ala Thr Leu Gly Gly Phe Gly
```

```
              340                 345                 350
Ser Leu Gly Leu Asp Cys Glu Pro Arg Thr Gly Leu Asp Phe Ser Asp
        355                 360                 365

Leu Tyr Tyr Leu Thr Met Asn Asn Lys His Trp Leu Val His Lys Glu
370                 375                 380

Trp Phe His Asp Ile Pro Leu Pro Trp His Ala Gly Ala Asp Thr Gly
385                 390                 395                 400

Thr Pro His Trp Asn Asn Lys Glu Ala Leu Val Glu Phe Lys Asp Ala
                405                 410                 415

His Ala Lys Arg Gln Thr Val Val Leu Gly Ser Gln Glu Gly Ala
            420                 425                 430

Val His Thr Ala Leu Ala Gly Ala Leu Glu Ala Glu Met Asp Gly Ala
        435                 440                 445

Lys Gly Arg Leu Ser Ser Gly His Leu Lys Cys Arg Leu Lys Met Asp
450                 455                 460

Lys Leu Arg Leu Lys Gly Val Ser Tyr Ser Leu Cys Thr Ala Ala Phe
465                 470                 475                 480

Thr Phe Thr Lys Ile Pro Ala Glu Thr Leu His Gly Thr Val Thr Val
                485                 490                 495

Glu Val Gln Tyr Ala Gly Thr Asp Gly Pro Cys Lys Val Pro Ala Gln
            500                 505                 510

Met Ala Val Asp Met Gln Thr Leu Thr Pro Val Gly Arg Leu Ile Thr
        515                 520                 525

Ala Asn Pro Val Ile Thr Glu Ser Thr Glu Asn Ser Lys Met Met Leu
530                 535                 540

Glu Leu Asp Pro Pro Phe Gly Asp Ser Tyr Ile Val Ile Gly Val Gly
545                 550                 555                 560

Glu Lys Lys Ile Thr His His Trp His Arg Ser Gly Ser Thr Ile Gly
                565                 570                 575

Lys Ala Phe Glu Ala Thr Val Arg Gly Ala Lys Arg Met Ala Val Leu
            580                 585                 590

Gly Asp Thr Ala Trp Asp Phe Gly Ser Val Gly Gly Ala Leu Asn Ser
        595                 600                 605

Leu Gly Lys Gly Ile His Gln Ile Phe Gly Ala Ala Phe Lys Ser Leu
610                 615                 620

Phe Gly Gly Met Ser Trp Phe Ser Gln Ile Leu Ile Gly Thr Leu Leu
625                 630                 635                 640

Met Trp Leu Gly Leu Asn Thr Lys Asn Gly Ser Ile Ser Leu Met Cys
                645                 650                 655

Leu Ala Leu Gly Gly Val Leu Ile Phe Leu Ser Thr Ala Val Ser Ala
            660                 665                 670

Asp Val

<210> SEQ ID NO 8
<211> LENGTH: 13
<212> TYPE: DNA
<213> ORGANISM: Artificial Sequence
<220> FEATURE:
<223> OTHER INFORMATION: Kozak consensus sequence

<400> SEQUENCE: 8
gccgccgcca tgg                                                          13

<210> SEQ ID NO 9
<211> LENGTH: 43
```

```
<212> TYPE: PRT
<213> ORGANISM: Artificial Sequence
<220> FEATURE:
<223> OTHER INFORMATION: Synthetic polypeptide

<400> SEQUENCE: 9

Arg Lys Glu Lys Lys Arg Arg Gly Ala Asp Thr Ser Ile Gly Ile Val
1               5                   10                  15

Gly Leu Leu Leu Thr Thr Ala Met Ala Ala Glu Ile Thr Arg Arg Gly
                20                  25                  30

Ser Ala Tyr Tyr Met Tyr Leu Asp Arg Ser Asp
            35                  40

<210> SEQ ID NO 10
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 10

Gly Ala Asp Thr Ser Ile Gly Ile Val Gly Leu Leu Leu Thr Thr Ala
1               5                   10                  15

Met Ala Ala Glu Ile Thr Arg Arg Gly Ser Ala Tyr Tyr Met Tyr Leu
                20                  25                  30

Asp Arg Ser Asp
            35

<210> SEQ ID NO 11
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 11

Gly Ala Asp Thr Ser Ile Gly Ile Val Gly Leu Leu Leu Thr Thr Ala
1               5                   10                  15

Met Ala Ala Glu Val Thr Arg Arg Gly Ser Ala Tyr Tyr Met Tyr Leu
                20                  25                  30

Asp Arg Asn Asp
            35

<210> SEQ ID NO 12
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 12

Arg Lys Glu Lys Lys Arg Arg Gly Ala Asp Thr Ser Val Gly Ile Val
1               5                   10                  15

Gly Leu Leu Leu Thr Thr Ala Met Ala Ala Glu Val Thr Arg Arg Gly
                20                  25                  30

Ser Ala Tyr Tyr Met Tyr Leu Asp Arg Asn Asp
            35                  40

<210> SEQ ID NO 13
<211> LENGTH: 36
<212> TYPE: PRT
<213> ORGANISM: Artificial Sequence
<220> FEATURE:
```

```
<223> OTHER INFORMATION: Synthetic polypeptide

<400> SEQUENCE: 13

Gly Ala Asp Thr Ser Val Gly Ile Val Gly Leu Leu Leu Thr Thr Ala
1               5                   10                  15

Met Ala Ala Glu Val Thr Arg Arg Gly Ser Ala Tyr Tyr Met Tyr Leu
                20                  25                  30

Asp Arg Asn Asp
        35

<210> SEQ ID NO 14
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 14

Met Gly Lys Arg Ser Ala Gly Ser Ile Met Trp Leu Ala Ser Leu Ala
1               5                   10                  15

Val Val Ile Ala Gly Thr Ser Ala Ala Glu Ile Thr Arg Arg Gly Ser
                20                  25                  30

Ala Tyr Tyr Met Tyr Leu Asp Arg Ser Asp
        35                  40

<210> SEQ ID NO 15
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 15

Met Gly Lys Arg Ser Ala Gly Ser Ile Met Trp Leu Ala Ser Leu Ala
1               5                   10                  15

Val Val Ile Ala Gly Thr Ser Ala Ala Glu Val Thr Arg Arg Gly Ser
                20                  25                  30

Ala Tyr Tyr Met Tyr Leu Asp Arg Asn Asp
        35                  40

<210> SEQ ID NO 16
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 16

Met Gly Lys Arg Ser Ala Gly Ser Ile Met Trp Leu Ala Ser Leu Ala
1               5                   10                  15

Val Val Ile Ala Gly Thr Ser Ala Glu Val Thr Arg Arg Gly Ser Ala
                20                  25                  30

Tyr Tyr Met Tyr Leu Asp Arg Asn Asp
        35                  40

<210> SEQ ID NO 17
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 17
```

```
Met Gly Lys Arg Ser Ala Gly Ser Ile Met Trp Leu Ala Ser Leu Ala
1               5                   10                  15

Val Val Ile Ala Gly Thr Ser Ala Ala Glu Thr Arg Arg Gly Ser Ala
            20                  25                  30

Tyr Tyr Met Tyr Leu Asp Arg Asn Asp
        35                  40

<210> SEQ ID NO 18
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 18

Met Gly Lys Arg Ser Ala Gly Ser Ile Met Trp Leu Ala Ser Leu Ala
1               5                   10                  15

Val Val Ile Ala Gly Thr Ser Ala Ala Val Glu Val Thr Arg Arg Gly
            20                  25                  30

Ser Ala Tyr Tyr Met Tyr Leu Asp Arg Asn Asp
        35                  40

<210> SEQ ID NO 19
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 19

Met Gly Lys Arg Ser Ala Gly Ser Ile Met Trp Leu Ala Ser Leu Ala
1               5                   10                  15

Val Val Ile Ala Gly Thr Ser Ala Val Glu Val Thr Arg Arg Gly Ser
            20                  25                  30

Ala Tyr Tyr Met Tyr Leu Asp Arg Asn Asp
        35                  40

<210> SEQ ID NO 20
<211> LENGTH: 5328
<212> TYPE: DNA
<213> ORGANISM: Artificial Sequence
<220> FEATURE:
<223> OTHER INFORMATION: Plasmid construct pEZMRprME KD

<400> SEQUENCE: 20
ctttgtacaa aaaagcaggc ttcgaaggag atagaaccaa ttctctaagg aaatacttaa      60
ccatggtcga ctggatccgg taccgaattc gtcgactagc ccatatatgg agttccgcgt     120
tacataactt acggtaaatg gcccgcctgg ctgaccgccc aacgaccccc gcccattgac     180
gtcaataatg acgtatgttc ccatagtaac gccaataggg actttccatt gacgtcaatg     240
ggtggagtat ttacggtaaa ctgcccactt ggcagtacat caagtgtatc atatgccaag     300
tacgccccct attgacgtca atgacggtaa atggcccgcc tggcattatg cccagtacat     360
gaccttatgg gactttccta cttggcagta catctacgta ttagtcatcg ctattaccat     420
ggtgatgcgg ttttggcagt acatcaatgg gcgtggatag cggtttgact cacggggatt     480
tccaagtctc cacccattg acgtcaatgg gagtttgttt tggcaccaaa atcaacggga     540
ctttccaaaa tgtcgtaaca actccgcccc attgacgcaa atgggcggta ggcgtgtacg     600
gtgggaggtc tatataagca gagctctctg gctaactaga acccactg cttactggct     660
```

```
tatcgaaatt aatacgactc actatagggA gacccaagct ggctagcgtt taaacttaag    720
cttggtaccg ccgccgccat gggcaagagg tccgccggct caatcatgtg gctcgcgagc    780
ttggcagttg tcatagctgg tacaagcgct gcagagatca ctagacgcgg gagtgcatac    840
tacatgtact tggataggag cgatgccggg aaggccattt cgtttgctac cacattggga    900
gtgaacaagt gccacgtaca gatcatggac ctcgggcaca tgtgtgacgc caccatgagt    960
tatgagtgcc ctatgctgga tgagggagtg gaaccagatg atgtcgattg ctggtgcaac    1020
acgacatcaa cttgggttgt gtacggaacc tgtcatcaca aaaaaggtga ggcacggcga    1080
tctagaagag ccgtgacgct ccttctcac tctacgagga agttgcaaac gcggtcgcag      1140
acctggttag aatcaagaga atacacgaag cacttgatca aggttgaaaa ctggatattc    1200
aggaaccccg ggtttgcgct agtggccgtt gccattgcct ggcttttggg aagctcgacg    1260
agccaaaaag tcatatactt ggtcatgata ctgctgattg ccccggcata cagtatcagg    1320
tgcattggag tcagcaatag agacttcgtg gagggcatgt caggtgggac ctgggttgat    1380
gttgtcttgg aacatggagg ctgcgttacc gtgatggcac aggacaagcc aacagttgac    1440
atagagttgg tcacgacgac ggttagtaac atggccgagg taagatccta ttgctacgag    1500
gcatcgatat cggacatggc ttcggacagt cgttgcccaa cacaaggtga agcctacctt    1560
gacaagcaat cagacactca atatgtctgc aaaagaacat tagtggacag aggttgggga    1620
aacggttgta aggattttgg caagggagc ttggtgacat gtgccaagtt tacgtgttct     1680
aagaagatga ccgggaagag cattcaaccg gaaaatctgg agtatcggat aatgctatca    1740
gtgcatggct cccagcatag cgggatgatt gtcaatgata caggatatga aactgacgaa    1800
aatagagcga aagtcgaggt tacgcctaat tcaccaagag cggaagcaac cttgggaggc    1860
tttggaagct taggacttga ctgtgaacca aggacaggcc ttgactttc agatctgtat     1920 tacctgacca tgaacaataa gcattggttg gtgcacaaag agtggtttca tgacatccca    1980
ttgccttggc atgctggggc agacaccgga actccacact ggaacaacaa agaggcattg    2040
gtagaattca aggatgccca cgccaagagg caaaccgtcg tcgttctggg gagccaggaa    2100
ggagccgttc acacggctct cgctggagct ctagaggctg agatggatgg tgcaaaggga    2160
aagctgttct ctggccattt gaaatgccgc ctaaaaatgg acaagcttag attgaagggc    2220
gtgtcatatt ccttgtgcac tgcggcattc acattcacca aggtcccagc tgaaacactg    2280
catggaacag tcacagtgga ggtgcagtat gcagggacag atggaccctg caagatccca    2340
gtccagatgg cggtggacat gcagaccctg accccagttg gagggctgat aaccgccaac    2400
cccgtgatta ctgaaagcac tgagaactca agatgatgt tggagcttga cccaccattt    2460
ggggattctt acattgtcat aggagttggg gacaagaaaa tcacccacca ctggcatagg    2520
agtggtagca ccatcggaaa ggcatttgag gccactgtga gaggcgccaa gagaatggca    2580
gtcctggggg atacagcctg ggacttcgga tcagtcgggg gtgtgttcaa ctcactgggt    2640
aagggcattc accagatttt tggagcagcc ttcaaatcac tgtttggagg aatgtcctgg    2700
ttctcacaga tcctcatagg cacgctgcta gtgtggttag gtttgaacac aaagaatgga    2760
tctatctccc tcacatgctt ggccctgggg ggagtgatga tcttcctctc cacggctgtt    2820
tctgcttgag cggccgctcg agtctagagg gcccgtttaa acccgctgat cagcctcgac    2880
tgtgccttct agttgccagc catctgttgt ttgcccctcc ccgtgccttc cttgaccct     2940 ggaaggtgcc actcccactg tccttctccta ataaaatgag gaaattgcat cgcattgtct    3000
```

-continued

```
gagtaggtgt cattctattc tggggggtgg ggtggggcag gacagcaagg gggaggattg    3060
ggaagacaat agcaggcatg ctggggatgc ggtgggctct atggcttcta ctgggcggtt    3120
ttatggacag caagcgaacc ggaattgcca gctggggcgc cctctggtaa ggtgatatct    3180
agacccagct ttcttgtaca aagttggcat tataagaaag cattgcttat caatttgttg    3240
caacgaacag gtcactatca gtcaaaataa aatcattatt tgccatccag ctgcagctct    3300
ggcccgtgtc tcaaaatctc tgatgttaca ttgcacaaga taaaaatata tcatcatgaa    3360
caataaaact gtctgcttac ataaacagta atacaagggg tgttatgagc catattcaac    3420
gggaaacgtc gaggccgcga ttaaattcca acatggatgc tgatttatat gggtataaat    3480
gggctcgcga taatgtcggg caatcaggtg cgacaatcta tcgcttgtat gggaagcccg    3540
atgcgccaga gttgtttctg aaacatggca aaggtagcgt tgccaatgat gttacagatg    3600
agatggtcag actaaactgg ctgacggaat ttatgcctct tccgaccatc aagcatttta    3660
tccgtactcc tgatgatgca tggttactca ccactgcgat ccccggaaaa acagcattcc    3720
aggtattaga agaatatcct gattcaggtg aaaatattgt tgatgcgctg gcagtgttcc    3780
tgcgccggtt gcattcgatt cctgtttgta attgtccttt taacagcgat cgcgtatttc    3840
gtctcgctca ggcgcaatca cgaatgaata acggtttggt tgatgcgagt gattttgatg    3900
acgagcgtaa tggctggcct gttgaacaag tctggaaaga atgcataaa cttttgccat    3960
tctcaccgga ttcagtcgtc actcatggtg atttctcact tgataacctt attttttgacg    4020
aggggaaatt aataggttgt attgatgttg gacgagtcgg aatcgcagac cgataccagg    4080
atcttgccat cctatggaac tgcctcggtg agttttctcc ttcattacag aaacggcttt    4140
ttcaaaaata tggtattgat aatcctgata tgaataaatt gcagtttcat ttgatgctcg    4200
atgagttttt ctaatcagaa ttggttaatt ggttgtaaca ttattcagat tgggcccgt    4260
tccactgagc gtcagacccc gtagaaaaga tcaaaggatc ttcttgagat cctttttttc    4320
tgcgcgtaat ctgctgcttg caaacaaaaa aaccaccgct accagcggtg gtttgtttgc    4380
cggatcaaga gctaccaact cttttttccga aggtaactgg cttcagcaga gcgcagatac    4440
caaatactgt tcttctagtg tagccgtagt taggccacca cttcaagaac tctgtagcac    4500
cgcctacata cctcgctctg ctaatcctgt taccagtggc tgctgccagt ggcgataagt    4560
cgtgtcttac cgggttggac tcaagacgat agttaccgga taaggcgcag cggtcgggct    4620
gaacgggggg ttcgtgcaca cagcccagct tggagcgaac gacctacacc gaactgagat    4680
acctacagcg tgagctatga gaaagcgcca cgcttcccga agggagaaag gcggacaggt    4740
atccggtaag cggcagggtc ggaacaggag agcgcacgag ggagcttcca gggggaaacg    4800
cctggtatct ttatagtcct gtcgggtttc gccacctctg acttgagcgt cgatttttgt    4860
gatgctcgtc agggggggcgg agcctatgga aaaacgccag caacgcggcc ttttttacggt    4920
tcctggcctt ttgctggcct tttgctcaca tgttctttcc tgcgttatcc cctgattctg    4980
tggataaccg tattaccgct agcatggatc tcggggacgt ctaactacta agcgagagta    5040
gggaactgcc aggcatcaaa taaaacgaaa ggctcagtcg gaagactggg cctttcgttt    5100
tatctgttgt ttgtcggtga acgctctcct gagtaggaca aatccgccgg gagcggattt    5160
gaacgttgtg aagcaacggc ccggagggtg gcgggcagga cgcccgccat aaactgccag    5220
gcatcaaact aagcagaagg ccatcctgac ggatggcctt tttgcgtttc tacaaactct    5280
tcctgttagt tagttactta agctcgggcc ccaaataatg attttatt               5328
```

```
<210> SEQ ID NO 21
<211> LENGTH: 672
<212> TYPE: PRT
<213> ORGANISM: Artificial Sequence
<220> FEATURE:
<223> OTHER INFORMATION: Syntheric polypeptide

<400> SEQUENCE: 21

Ala Glu Ile Thr Arg Arg Gly Ser Ala Tyr Tyr Met Tyr Leu Asp Arg
1               5                   10                  15

Ser Asp Ala Gly Lys Ala Ile Ser Phe Ala Thr Thr Leu Gly Val Asn
            20                  25                  30

Lys Cys His Val Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Lys Val Glu Asn Trp
        115                 120                 125

Ile Phe Arg Asn Pro Gly Phe Ala Leu Val Ala Val Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser Ile Arg Cys Ile Gly Val Ser Asn
                165                 170                 175

Arg Asp Phe Val Glu Gly Met Ser Gly Gly Thr Trp Val Asp Val Val
            180                 185                 190

Leu Glu His Gly Gly Cys Val Thr Val Met Ala Gln Asp Lys Pro Thr
        195                 200                 205

Val Asp Ile Glu Leu Val Thr Thr Thr Val Ser Asn Met Ala Glu Val
    210                 215                 220

Arg Ser Tyr Cys Tyr Glu Ala Ser Ile Ser Asp Met Ala Ser Asp Ser
225                 230                 235                 240

Arg Cys Pro Thr Gln Gly Glu Ala Tyr Leu Asp Lys Gln Ser Asp Thr
                245                 250                 255

Gln Tyr Val Cys Lys Arg Thr Leu Val Asp Arg Gly Trp Gly Asn Gly
            260                 265                 270

Cys Lys Asp Phe Gly Lys Gly Ser Leu Val Thr Cys Ala Lys Phe Thr
        275                 280                 285

Cys Ser Lys Lys Met Thr Gly Lys Ser Ile Gln Pro Glu Asn Leu Glu
    290                 295                 300

Tyr Arg Ile Met Leu Ser Val His Gly Ser Gln His Ser Gly Met Ile
305                 310                 315                 320

Val Asn Asp Thr Gly Tyr Glu Thr Asp Glu Asn Arg Ala Lys Val Glu
                325                 330                 335

Val Thr Pro Asn Ser Pro Arg Ala Glu Ala Thr Leu Gly Gly Phe Gly
            340                 345                 350

Ser Leu Gly Leu Asp Cys Glu Pro Arg Thr Gly Leu Asp Phe Ser Asp
        355                 360                 365

Leu Tyr Tyr Leu Thr Met Asn Asn Lys His Trp Leu Val His Lys Glu
```

```
                370             375             380
Trp Phe His Asp Ile Pro Leu Pro Trp His Ala Gly Ala Asp Thr Gly
385             390             395             400

Thr Pro His Trp Asn Asn Lys Glu Ala Leu Val Glu Phe Lys Asp Ala
            405             410             415

His Ala Lys Arg Gln Thr Val Val Leu Gly Ser Gln Glu Gly Ala
        420             425             430

Val His Thr Ala Leu Ala Gly Ala Leu Glu Ala Glu Met Asp Gly Ala
            435             440             445

Lys Gly Lys Leu Phe Ser Gly His Leu Lys Cys Arg Leu Lys Met Asp
    450             455             460

Lys Leu Arg Leu Lys Gly Val Ser Tyr Ser Leu Cys Thr Ala Ala Phe
465             470             475             480

Thr Phe Thr Lys Val Pro Ala Glu Thr Leu His Gly Thr Val Thr Val
                485             490             495

Glu Val Gln Tyr Ala Gly Thr Asp Gly Pro Cys Lys Ile Pro Val Gln
            500             505             510

Met Ala Val Asp Met Gln Thr Leu Thr Pro Val Gly Leu Ile Thr
    515             520             525

Ala Asn Pro Val Ile Thr Glu Ser Thr Glu Asn Ser Lys Met Met Leu
530             535             540

Glu Leu Asp Pro Pro Phe Gly Asp Ser Tyr Ile Val Ile Gly Val Gly
545             550             555             560

Asp Lys Lys Ile Thr His His Trp His Arg Ser Gly Ser Thr Ile Gly
                565             570             575

Lys Ala Phe Glu Ala Thr Val Arg Gly Ala Lys Arg Met Ala Val Leu
            580             585             590

Gly Asp Thr Ala Trp Asp Phe Gly Ser Val Gly Gly Val Phe Asn Ser
        595             600             605

Leu Gly Lys Gly Ile His Gln Ile Phe Gly Ala Ala Phe Lys Ser Leu
    610             615             620

Phe Gly Gly Met Ser Trp Phe Ser Gln Ile Leu Ile Gly Thr Leu Leu
625             630             635             640

Val Trp Leu Gly Leu Asn Thr Lys Asn Gly Ser Ile Ser Leu Thr Cys
                645             650             655

Leu Ala Leu Gly Gly Val Met Ile Phe Leu Ser Thr Ala Val Ser Ala
            660             665             670

<210> SEQ ID NO 22
<211> LENGTH: 5334
<212> TYPE: DNA
<213> ORGANISM: Artificial Sequence
<220> FEATURE:
<223> OTHER INFORMATION: Plasmid construct pEBZHu2-3 KD

<400> SEQUENCE: 22
ctttgtacaa aaaagcaggc ttcgaaggag atagaaccaa ttctctaagg aaatacttaa      60
ccatggtcga ctggatccgg taccgaattc gtcgactagc ccatatatgg agttccgcgt     120
tacataactt acggtaaatg gcccgcctgg ctgaccgccc aacgaccccc gcccattgac     180
gtcaataatg acgtatgttc ccatagtaac gccaataggg actttccatt gacgtcaatg     240
ggtggagtat ttacggtaaa ctgcccactt ggcagtacat caagtgtatc atatgccaag     300
tacgccccct attgacgtca atgacggtaa atggcccgcc tggcattatg cccagtacat     360
gaccttatgg gactttccta cttggcagta catctacgta ttagtcatcg ctattaccat     420
```

```
ggtgatgcgg ttttggcagt acatcaatgg gcgtggatag cggtttgact cacgggatt      480 tccaagtctc caccccattg acgtcaatgg gagtttgttt tggcaccaaa atcaacggga     540
ctttccaaaa tgtcgtaaca actccgcccc attgacgcaa atgggcggta ggcgtgtacg     600
gtgggaggtc tatataagca gagctctctg gctaactaga aacccactg cttactggct      660 tatcgaaatt aatacgactc actataggga gacccaagct ggctagcgtt taaacttaag     720
cttggtaccg ccgccgccat gggcaagagg tccgccggct caatcatgtg gctcgcgagc     780
ttggcagttg tcatagctgg tacaagcgcc gtggaagtga ccagaagagg cagcgcctac     840
tacatgtacc tggaccggaa cgatgccggc gaggccatca gctttccaac cacccctggc     900
atgaacaagt gctacatcca gatcatggac ctgggccaca tgtgcgacgc caccatgagc     960
tacgagtgcc ccatgctgga cgagggcgtg aacccgacg atgtggactg ctggtgcaac     1020
accaccagca cctgggtggt gtacggcacc tgtcaccaca agaagggcga agccagacgg     1080
tccagacggg ccgtgacact gcctagccac agcaccagaa agctgcagac ccggtcccag     1140
acctggctgg aaagcagaga gtacaccaag cacctgatcc gggtggaaaa ctggatcttc     1200
cggaaccccg gctttgccct ggccgctgct gctattgctt ggctgctggg cagcagcacc     1260
tcccagaaag tgatctacct cgtgatgatc ctgctgatcg cccctgccta cagcatccgg     1320
tgtatcggcg tgtccaaccg ggacttcgtg gaaggcatga gcggcggcac atgggtggac     1380
atcgtgctgg aacacggcgg ctgcgtgaca gtgatggccc aggataagcc caccgtggac     1440
attgagctcg tgaccaccac cgtgtccaat atggccgaag tgcggagcta ctgctacgag     1500
gccagcatca gcgacatggc cagcgacagc agatgcccca cagggcga ggcttacctg       1560 gacaagcagt ccgacaccca gtacgtgtgc aagcggaccc tggtggatag aggctggggc     1620
aatggctgca aggattttgg caagggcagc ctcgtgacct gcgccaagtt cgcctgcagc     1680
aagaagatga ccggcaagag catccagccc gagaacctgg aataccggat catgctgagc     1740
gtgcacggca gccagcactc cggcatgatc gtgaacgaca ccggccacga gacagacgag     1800
aaccgggcca aggtggaaat cacccccaac agccctagag ccgaggccac actgggcggc     1860
tttggatctc tgggcctgga ctgcgagcct agaaccggcc tggatttcag cgacctgtac     1920
tacctgacca tgaacaacaa gcactggctg gtgcacaaag agtggttcca cgacatcccc     1980
ctgccctggc atgccggcgc tgatacaggc acaccccact ggaacaacaa agaggctctg     2040
gtggagttca aggacgccca cgccaagagg cagaccgtgg tggtgctggg atctcaggaa     2100
ggcgccgtgc atacagctct ggctggcgcc ctggaagccg aaatggatgg cgctaagggc     2160
agactgtcca gcggccacct gaagtgccgg ctgaagatgg acaagctgcg gctgaagggc     2220
gtgtcctaca gcctgtgtac cgccgccttc accttcacca agatccccgc cgagacactg     2280
cacggcaccg tgactgtgga agtgcagtac gccggcaccg acggcccttg taagtgcct     2340 gctcagatgg ccgtggatat gcagaccctg accctgtgg gcaggctgat caccgccaac     2400
cctgtgatca ccgagagcac cgagaacagc aagatgatgc tggaactgga ccccccttc     2460 ggcgactcct acatcgtgat cggcgtggga gagaagaaga tcacccacca ctggcacaga     2520
agcggcagca ccatcggcaa agccttcgaa gccacagtgc ggggagccaa gagaatggcc     2580
gtgctgggag ataccgcctg ggactttggc tctgtgggcg agccctgaa ctctctgggc      2640 aagggaatcc accagatctt cggagccgcc tttaagagcc tgttcggcgg catgagctgg     2700
ttcagccaga tcctgatcgg caccctgctg atgtggctgg gcctgaacac caagaacggc     2760
```

```
agcatctccc tgatgtgcct ggctctggga ggcgtgctga tcttcctgag cacagccgtg    2820
tctgccgacg tgtgagcggc cgctcgagtc tagagggccc gtttaaaccc gctgatcagc    2880
ctcgactgtg ccttctagtt gccagccatc tgttgtttgc ccctcccccg tgccttcctt    2940
gaccctggaa ggtgccactc ccactgtcct ttcctaataa aatgaggaaa ttgcatcgca    3000
ttgtctgagt aggtgtcatt ctattctggg gggtggggtg gggcaggaca gcaaggggga    3060
ggattgggaa gacaatagca ggcatgctgg ggatgcggtg ggctctatgg cttctactgg    3120
gcggttttat ggacagcaag cgaaccggaa ttgccagctg gggcgccctc tggtaaggtg    3180
atatctagac ccagctttct tgtacaaagt tggcattata agaaagcatt gcttatcaat    3240
ttgttgcaac gaacaggtca ctatcagtca aaataaaatc attatttgcc atccagctgc    3300
agctctggcc cgtgtctcaa aatctctgat gttacattgc acaagataaa aatatatcat    3360
catgaacaat aaaactgtct gcttacataa acagtaatac aagggggtgtt atgagccata    3420 ttcaacggga aacgtcgagg ccgcgattaa attccaacat ggatgctgat ttatatgggt    3480
ataaatgggc tcgcgataat gtcgggcaat caggtgcgac aatctatcgc ttgtatggga    3540
agcccgatgc gccagagttg tttctgaaac atggcaaagg tagcgttgcc aatgatgtta    3600
cagatgagat ggtcagacta aactggctga cggaatttat gcctcttccg accatcaagc    3660
attttatccg tactcctgat gatgcatggt tactcaccac tgcgatcccc ggaaaaacag    3720
cattccaggt attagaagaa tatcctgatt caggtgaaaa tattgttgat gcgctggcag    3780
tgttcctgcg ccggttgcat tcgattcctg tttgtaattg tccttttaac agcgatcgcg    3840
tatttcgtct cgctcaggcg caatcacgaa tgaataacgg tttggttgat gcgagtgatt    3900
ttgatgacga gcgtaatggc tggcctgttg aacaagtctg gaaagaaatg cataaacttt    3960
tgccattctc accggattca gtcgtcactc atggtgattt ctcacttgat aaccttattt    4020
ttgacgaggg gaaattaata ggttgtattg atgttggacg agtcggaatc gcagaccgat    4080
accaggatct tgccatccta tggaactgcc tcggtgagtt ttctccttca ttacagaaac    4140
ggctttttca aaaatatggt attgataatc ctgatatgaa taaattgcag tttcatttga    4200
tgctcgatga gttttctaa tcagaattgg ttaattggtt gtaacattat tcagattggg    4260
ccccgttcca ctgagcgtca gaccccgtag aaaagatcaa aggatcttct tgagatcctt    4320 ttttttctgcg cgtaatctgc tgcttgcaaa caaaaaaacc accgctacca gcggtggttt    4380
gtttgccgga tcaagagcta ccaactcttt ttccgaaggt aactggcttc agcagagcgc    4440
agataccaaa tactgttctt ctagtgtagc cgtagttagg ccaccacttc aagaactctg    4500
tagcaccgcc tacatacctc gctctgctaa tcctgttacc agtggctgct gccagtggcg    4560
ataagtcgtg tcttacccgg ttggactcaa gacgatagtt accggataag gcgcagcggt    4620
cgggctgaac ggggggttcg tgcacacagc ccagcttgga gcgaacgacc tacaccgaac    4680
tgagatacct acagcgtgag ctatgagaaa gcgccacgct tcccgaaggg agaaaggcgg    4740
acaggtatcc ggtaagcggc agggtcggaa caggagagcg cacgagggag cttccagggg    4800
gaaacgcctg gtatctttat agtcctgtcg ggtttcgcca cctctgactt gagcgtcgat    4860
ttttgtgatg ctcgtcaggg gggcggagcc tatggaaaaa cgccagcaac gcggcctttt    4920
tacggttcct ggccttttgc tggccttttg ctcacatgtt ctttcctgcg ttatcccctg    4980
attctgtgga taaccgtatt accgctagca tggatctcgg ggacgtctaa ctactaagcg    5040
agagtaggga actgccaggc atcaaataaa acgaaaggct cagtcggaag actgggcctt    5100
tcgttttatc tgttgtttgt cggtgaacgc tctcctgagt aggacaaatc cgccgggagc    5160
```

-continued

```
ggatttgaac gttgtgaagc aacggcccgg agggtggcgg gcaggacgcc cgccataaac    5220
tgccaggcat caaactaagc agaaggccat cctgacggta ggcctttttg cgtttctaca    5280
aactcttcct gttagttagt tacttaagct cgggcccca ataatgattt tatt          5334
```

<210> SEQ ID NO 23
<211> LENGTH: 674
<212> TYPE: PRT
<213> ORGANISM: Artificial Sequence
<220> FEATURE:
<223> OTHER INFORMATION: Synthetic polypeptide

<400> SEQUENCE: 23

```
Val Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Arg Val Glu Asn Trp
        115                 120                 125

Ile Phe Arg Asn Pro Gly Phe Ala Leu Ala Ala Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser Ile Arg Cys Ile Gly Val Ser Asn
                165                 170                 175

Arg Asp Phe Val Glu Gly Met Ser Gly Gly Thr Trp Val Asp Ile Val
            180                 185                 190

Leu Glu His Gly Gly Cys Val Thr Val Met Ala Gln Asp Lys Pro Thr
        195                 200                 205

Val Asp Ile Glu Leu Val Thr Thr Thr Val Ser Asn Met Ala Glu Val
    210                 215                 220

Arg Ser Tyr Cys Tyr Glu Ala Ser Ile Ser Asp Met Ala Ser Asp Ser
225                 230                 235                 240

Arg Cys Pro Thr Gln Gly Glu Ala Tyr Leu Asp Lys Gln Ser Asp Thr
                245                 250                 255

Gln Tyr Val Cys Lys Arg Thr Leu Val Asp Arg Gly Trp Gly Asn Gly
            260                 265                 270

Cys Lys Asp Phe Gly Lys Gly Ser Leu Val Thr Cys Ala Lys Phe Ala
        275                 280                 285

Cys Ser Lys Lys Met Thr Gly Lys Ser Ile Gln Pro Glu Asn Leu Glu
    290                 295                 300

Tyr Arg Ile Met Leu Ser Val His Gly Ser Gln His Ser Gly Met Ile
305                 310                 315                 320

Val Asn Asp Thr Gly His Glu Thr Asp Glu Asn Arg Ala Lys Val Glu
                325                 330                 335
```

```
Ile Thr Pro Asn Ser Pro Arg Ala Glu Ala Thr Leu Gly Gly Phe Gly
            340                 345                 350

Ser Leu Gly Leu Asp Cys Glu Pro Arg Thr Gly Leu Asp Phe Ser Asp
        355                 360                 365

Leu Tyr Tyr Leu Thr Met Asn Asn Lys His Trp Leu Val His Lys Glu
    370                 375                 380

Trp Phe His Asp Ile Pro Leu Pro Trp His Ala Gly Ala Asp Thr Gly
385                 390                 395                 400

Thr Pro His Trp Asn Asn Lys Glu Ala Leu Val Glu Phe Lys Asp Ala
            405                 410                 415

His Ala Lys Arg Gln Thr Val Val Leu Gly Ser Gln Glu Gly Ala
        420                 425                 430

Val His Thr Ala Leu Ala Gly Ala Leu Glu Ala Glu Met Asp Gly Ala
    435                 440                 445

Lys Gly Arg Leu Ser Ser Gly His Leu Lys Cys Arg Leu Lys Met Asp
    450                 455                 460

Lys Leu Arg Leu Lys Gly Val Ser Tyr Ser Leu Cys Thr Ala Ala Phe
465                 470                 475                 480

Thr Phe Thr Lys Ile Pro Ala Glu Thr Leu His Gly Thr Val Thr Val
            485                 490                 495

Glu Val Gln Tyr Ala Gly Thr Asp Gly Pro Cys Lys Val Pro Ala Gln
        500                 505                 510

Met Ala Val Asp Met Gln Thr Leu Thr Pro Val Gly Arg Leu Ile Thr
    515                 520                 525

Ala Asn Pro Val Ile Thr Glu Ser Thr Glu Asn Ser Lys Met Met Leu
    530                 535                 540

Glu Leu Asp Pro Pro Phe Gly Asp Ser Tyr Ile Val Ile Gly Val Gly
545                 550                 555                 560

Glu Lys Lys Ile Thr His His Trp His Arg Ser Gly Ser Thr Ile Gly
            565                 570                 575

Lys Ala Phe Glu Ala Thr Val Arg Gly Ala Lys Arg Met Ala Val Leu
        580                 585                 590

Gly Asp Thr Ala Trp Asp Phe Gly Ser Val Gly Gly Ala Leu Asn Ser
    595                 600                 605

Leu Gly Lys Gly Ile His Gln Ile Phe Gly Ala Ala Phe Lys Ser Leu
    610                 615                 620

Phe Gly Gly Met Ser Trp Phe Ser Gln Ile Leu Ile Gly Thr Leu Leu
625                 630                 635                 640

Met Trp Leu Gly Leu Asn Thr Lys Asn Gly Ser Ile Ser Leu Met Cys
            645                 650                 655

Leu Ala Leu Gly Gly Val Leu Ile Phe Leu Ser Thr Ala Val Ser Ala
        660                 665                 670

Asp Val

<210> SEQ ID NO 24
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 24
caatggctgc aaggactttg gcaagggcag cc                                    32
```

```
<210> SEQ ID NO 25
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 25
caatggctgc cgagactttg gcaagggcag cctcg                              35

<210> SEQ ID NO 26
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 26
caatggctgc cgacattttg gcaagggcag cc                                 32

<210> SEQ ID NO 27
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 27
caatggctgc gaagattttg gcaagggcag                                    30

<210> SEQ ID NO 28
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 28
caatggctgc gaacgatttg gcaagggcag c                                  31

<210> SEQ ID NO 29
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 29
gaaacggttg taaggatttt ggcaaaggga g                                  31
```